(12) United States Patent
Hutchison et al.

(10) Patent No.: US 8,403,044 B2
(45) Date of Patent: Mar. 26, 2013

(54) SULFONATED INTERNAL OLEFIN SURFACTANT FOR ENHANCED OIL RECOVERY

(75) Inventors: John C. Hutchison, Chicago, IL (US);
Patrick Shane Wolfe, Palatine, IL (US);
Thomas Edward Waldman, Aurora, CO (US); Ramakrishna Ravikiran, Centennial, CO (US)

(73) Assignee: Stepan Company, Northfield, IL (US)

( * ) Notice: Subject to any disclaimer, the term of this patent is extended or adjusted under 35 U.S.C. 154(b) by 324 days.

(21) Appl. No.: 12/800,000

(22) Filed: May 5, 2010

(65) Prior Publication Data

US 2010/0282467 A1    Nov. 11, 2010

Related U.S. Application Data

(60) Provisional application No. 61/215,513, filed on May 5, 2009.

(51) Int. Cl.
*E21B 43/22*    (2006.01)
(52) U.S. Cl. .................. 166/270.1; 166/300; 166/305.1; 166/371
(58) Field of Classification Search .......................... None
See application file for complete search history.

(56) References Cited

U.S. PATENT DOCUMENTS

| | | |
|---|---|---|
| 3,424,694 A | 1/1969 | Stein et al. |
| 3,506,070 A | 4/1970 | Jones |
| 3,613,786 A | 10/1971 | Jones et al. |
| 3,647,906 A | 3/1972 | Farley |
| 3,740,343 A | 6/1973 | Jones et al. |
| 3,943,160 A | 3/1976 | Farmer, III et al. |
| 3,946,812 A | 3/1976 | Gale et al. |
| 3,983,940 A | 10/1976 | Carpenter, Jr. et al. |
| 3,990,515 A | 11/1976 | Wilchester et al. |
| 4,017,405 A | 4/1977 | Holm |
| 4,018,278 A | 4/1977 | Shupe |
| 4,059,154 A | 11/1977 | Braden, Jr. et al. |
| 4,066,124 A | 1/1978 | Carlin et al. |
| 4,077,471 A | 3/1978 | Shupe et al. |
| 4,125,156 A | 11/1978 | Glinsmann |
| 4,183,867 A | 1/1980 | Sekiguchi et al. |
| 4,216,079 A | 8/1980 | Newcombe |
| 4,248,793 A | 2/1981 | Sekiguchi et al. |
| 4,252,192 A | 2/1981 | Nussbaum et al. |
| 4,265,308 A | 5/1981 | Hedges et al. |
| 4,532,053 A | 7/1985 | Morita et al. |
| 4,534,411 A | 8/1985 | Morita et al. |
| 4,549,607 A | 10/1985 | Morita et al. |
| 4,555,351 A | 11/1985 | Morita et al. |
| 4,556,108 A | 12/1985 | Morita et al. |
| 4,597,879 A | 7/1986 | Morita et al. |
| 4,727,203 A | 2/1988 | Hamilton, Jr. |
| 4,733,728 A | 3/1988 | Morita et al. |
| 4,765,408 A | 8/1988 | Morita et al. |
| 4,895,997 A | 1/1990 | Hamilton, Jr. et al. |
| 4,981,176 A | 1/1991 | Hurd |
| 5,076,357 A | 12/1991 | Marquis |
| 5,077,414 A | 12/1991 | Arduengo, III |
| 5,103,909 A | 4/1992 | Morgenthaler et al. |
| 5,182,405 A | 1/1993 | Arduengo, III |
| 5,199,490 A | 4/1993 | Surles et al. |
| 5,203,411 A | 4/1993 | Dawe et al. |
| 5,246,072 A | 9/1993 | Frazier, Jr. et al. |
| 5,247,993 A | 9/1993 | Sarem et al. |
| 5,284,206 A | 2/1994 | Surles et al. |
| 5,318,709 A | 6/1994 | Wuest et al. |
| 5,342,909 A | 8/1994 | Grubbs et al. |
| 5,411,094 A | 5/1995 | Northrop |
| 5,654,261 A | 8/1997 | Smith |
| 5,710,298 A | 1/1998 | Grubbs et al. |
| 5,723,423 A | 3/1998 | Van Slyke |
| 5,728,839 A | 3/1998 | Herrmann et al. |
| 5,728,917 A | 3/1998 | Grubbs et al. |
| 5,750,815 A | 5/1998 | Grubbs et al. |
| 5,831,108 A | 11/1998 | Grubbs et al. |
| 5,849,974 A | 12/1998 | Clarembeau et al. |
| 6,175,047 B1 | 1/2001 | Hori et al. |

(Continued)

FOREIGN PATENT DOCUMENTS

| | | |
|---|---|---|
| DE | 19610908 A1 | 9/1997 |
| EP | 0351928 A1 | 1/1990 |

(Continued)

OTHER PUBLICATIONS

Rouhi, A. Maureen, Olefin Metathiesis: Big-Deal Reaction, Chemical & Engineering News, Dec. 23, 2002, pp. 29-33, vol. 80, No. 51, American Chemical Society, USA.

(Continued)

*Primary Examiner* — Zakiya W Bates
(74) *Attorney, Agent, or Firm* — Dilworth IP LLC

(57) ABSTRACT

A process for recovering oil from an oil-bearing formation comprises introducing into said formation an aqueous composition comprising at least one sulfonated derivative of one or more internal olefins, said internal olefins being characterized by having low amounts of tri-substitution on the olefin bond, said sulfonated derivative being obtained by sulfonating a composition comprising internal olefins of the formula:

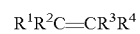

$R^1R^2C=CR^3R^4$ wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44 with the proviso that at least about 96 mole percent of $R^1$ and $R^3$ are straight- or branched-chain, saturated hydrocarbyl groups and at least about 96 mole percent of $R^2$ and $R^4$ are hydrogen. Further provided are compositions for use in recovering oil from an oil-bearing formation which comprise the sulfonated derivatives of one or more internal olefins having low amounts of tri-substitution on the olefin bond.

37 Claims, 15 Drawing Sheets

U.S. PATENT DOCUMENTS

| | | | |
|---|---|---|---|
| 6,177,575 B1 | 1/2001 | Arduengo, III et al. |
| 6,269,881 B1 | 8/2001 | Chou et al. |
| 6,281,404 B1 | 8/2001 | Miller |
| 6,306,988 B1 | 10/2001 | Grubbs et al. |
| 6,414,097 B1 | 7/2002 | Grubbs et al. |
| 6,506,944 B1 | 1/2003 | Schwab et al. |
| 6,552,139 B1 | 4/2003 | Herrmann et al. |
| 6,566,319 B1 | 5/2003 | Scheibel et al. |
| 6,605,748 B2 | 8/2003 | Wagener et al. |
| 6,777,584 B2 | 8/2004 | Patil et al. |
| 6,787,620 B2 | 9/2004 | Herrmann et al. |
| 6,888,002 B2 | 5/2005 | Herrmann et al. |
| 6,946,533 B2 | 9/2005 | Grubbs et al. |
| 7,034,096 B2 | 4/2006 | Choi et al. |
| 7,055,602 B2 | 6/2006 | Shpakoff et al. |
| 7,102,047 B2 | 9/2006 | Grubbs et al. |
| 7,137,447 B2 | 11/2006 | Shpakoff et al. |
| 7,229,950 B2 | 6/2007 | Shpakoff et al. |
| 7,262,153 B2 | 8/2007 | Shpakoff et al. |
| 7,288,666 B2 | 10/2007 | Grubbs et al. |
| 7,294,717 B2 | 11/2007 | Herrmann et al. |
| 7,329,758 B1 | 2/2008 | Grubbs et al. |
| 7,342,136 B2 | 3/2008 | Kenneally et al. |
| 7,365,140 B2 | 4/2008 | Piers et al. |
| 7,378,528 B2 | 5/2008 | Herrmann et al. |
| 7,449,596 B2 | 11/2008 | Campbell et al. |
| 7,468,343 B2 | 12/2008 | Campbell et al. |
| 7,495,140 B2 | 2/2009 | Campbell et al. |
| 7,581,594 B2 | 9/2009 | Tang |
| 7,598,330 B2 | 10/2009 | Grubbs et al. |
| 7,622,590 B1 | 11/2009 | Nolan et al. |
| 7,629,299 B2 | 12/2009 | Berger et al. |
| 7,652,145 B2 | 1/2010 | Herrmann et al. |
| 2003/0055262 A1 | 3/2003 | Grubbs et al. |
| 2003/0100776 A1 | 5/2003 | Grubbs et al. |
| 2003/0135080 A1 | 7/2003 | Botha et al. |
| 2003/0163011 A1 | 8/2003 | Wurziger et al. |
| 2003/0220512 A1 | 11/2003 | Blechert |
| 2003/0236427 A1 | 12/2003 | Grubbs et al. |
| 2004/0097745 A9 | 5/2004 | Grubbs et al. |
| 2004/0176608 A1 | 9/2004 | Blechert et al. |
| 2004/0177958 A1 | 9/2004 | Shpakoff et al. |
| 2005/0085397 A1 | 4/2005 | Hou et al. |
| 2005/0261451 A1 | 11/2005 | Ung et al. |
| 2007/0155975 A1 | 7/2007 | Grubbs et al. |
| 2007/0225536 A1 | 9/2007 | Lutz |
| 2007/0282148 A1 | 12/2007 | Berlin et al. |
| 2008/0064891 A1 | 3/2008 | Lee |
| 2008/0132708 A1 | 6/2008 | Grubbs et al. |
| 2008/0161210 A1 | 7/2008 | Welton et al. |
| 2008/0161212 A1 | 7/2008 | Welton et al. |
| 2008/0228017 A1 | 9/2008 | Burdett et al. |
| 2009/0012248 A1 | 1/2009 | Grubbs et al. |
| 2009/0012254 A1 | 1/2009 | Grubbs et al. |
| 2009/0111717 A1 | 4/2009 | Campbell et al. |
| 2009/0155866 A1 | 6/2009 | Burk et al. |
| 2009/0264672 A1 | 10/2009 | Abraham et al. |
| 2009/0305913 A1 | 12/2009 | Welton et al. |

FOREIGN PATENT DOCUMENTS

| | | |
|---|---|---|
| EP | 0446971 A1 | 9/1991 |
| EP | 0482687 A1 | 4/1992 |
| EP | 0351928 B1 | 6/1993 |
| EP | 0482687 B1 | 6/1996 |
| EP | 0721953 B1 | 4/2002 |
| EP | 1180108 B1 | 8/2003 |
| EP | 0842200 B1 | 3/2004 |
| EP | 0942914 B1 | 7/2005 |
| EP | 1375506 B1 | 4/2006 |
| EP | 0837885 B1 | 3/2008 |
| EP | 1180107 B1 | 6/2008 |
| GB | 2135713 A | 9/1984 |
| GB | 2168094 A | 6/1986 |
| WO | WO 00/15339 | 3/2000 |
| WO | WO 2004/101473 A2 | 11/2004 |
| WO | WO 2006/132902 A2 | 12/2006 |
| WO | WO 2006/132902 A3 | 12/2006 |
| WO | WO 2008/021883 A1 | 2/2008 |
| WO | WO 2008/042289 A2 | 4/2008 |
| WO | WO 2008/046106 A2 | 4/2008 |
| WO | WO 2008/079852 A1 | 7/2008 |
| WO | WO 2008/081158 A2 | 7/2008 |

OTHER PUBLICATIONS

Fox et al., Coupling of Terminal Olefins by Molybdenum (VI) Imido Alkylidene Complexes, Organometallics, 1994, pp. 635-639, vol. 13, No. 2, American Chemical Society, USA.

Spronk et al., Metathesis of 1-alkenes in the liquid phase over a Re207/γ-Al203 catalyst, Applied Catalysis, 1991, pp. 295-306, 70, Elsevier Science Publishers B. V., Amsterdam.

Doyle, G., Olefin Metathesis Catalyzed by Zero-Valent, Anionic Group VI Metal Compounds, Journal of Catalysis, 1973, pp. 118-127 vol. 30, Academic Press, Inc. USA.

Gibson et al., Novel Synthesis of Long-Chain Primary Alkyl Compounds, J. Org. Chem., 1981, pp. 1821-1823, vol. 46, No. 9, American Chemical Society, USA.

Gupta, et al., Micellar Flooding—Compositional Effects on Oil Displacement, Society of Petroleum Engineers Journal, 1979, pp. 116-128, Society of Petroleum Engineers of AIME.

Zhao, et al., Development of High-Performance Surfactants for Difficult Oils, SPE International 113432, 2008, pp. 1-11, Society of Petroleum Engineers, USA.

Zhang, et al., Mechanisms of Enhanced Natural Imbibition with Novel Chemicals, SPE International 113453, 2008, pp. 1-12, Society of Petroleum Engineers, USA.

Ivin, K.J., and Mol, J.C., Olefin Metathesis and Metathesis Polymerization, pp. 400-401, Academic Press.

Healy, et al., Multiphase Microemulsion Systems, Society of Petroleum Engineers Journal, Jun. 1976, pp. 147-160, American Institute of Mining, Metallurgical, & Petroleum Eng.

Levitt, David B., Experimental Evaluation of High Performance EOR Surfactants for a Dolomite Oil Reservoir, M.S. Thesis, Dec. 2006, pp. v-19, University of Texas at Austin.

Falls, A.H., et al., Field Test of Cosurfactant-Enhanced Alkaline Flooding, SPE Reservoir Engineering, Aug. 1994, pp. 217-223, Society of Petroleum Engineers, USA.

Sanz, C.A., et al., Alcohol-Free Chemical Flooding: From Surfactant Screening to Coreflood Design, SPE 28956, SPE International, 1995, p. 117-128, SPE, Inc., USA.

Levitt, David B., et al., Identification and Evaluation of High Performance EOR Surfactants, SPE 100089, SPE International, 2006, p. 1-11, Society of Petroleum Engineers, USA.

Freitas, E.R., et al., Shell's Higher Olefins Process, CEP, Jan. 1979, p. 73-76, AIChE, USA.

Radici, P. et al., Internal n-olefin sulphonates, Tenside, surfactants, detergents, XXIII XED, Barcelona, Espagne (Dec. 3, 1992) 1994, vol. 31, No. 5, pp. 299-307 (20 ref.).

Barnes, J. R., et al., Application of Internal Olefin Sulfonates & Other Surfactants to EOR., SPE 129766, SPE International, 2010, p. 1-16, Society of Petroleum Engineers, US.

Hirasaki, G.J., et al., Recent Advances in Surfactant EOR, SPE 115386 (revised) IPTC, 2008 p. 1-35, Society of Petroleum Engineers, USA.

International Search Report mailed Aug. 16, 2010 in PCT/US2010/001337.

Written Opinion of the International Searching Authority mailed Aug. 16, 2010 in PCT/US2010/001337.

SULFONATED INTERNAL OLEFIN SURFACTANT FOR ENHANCED OIL RECOVERY

FIELD OF THE INVENTION

This disclosure relates to a process for enhanced oil recovery and to compositions useful therein. More particularly, this disclosure relates to a process for enhanced oil recovery which employs a sulfonated internal olefin surfactant and to an enhanced oil recovery composition comprising the sulfonated internal olefin surfactant.

BACKGROUND OF THE INVENTION

Crude oil development and production from oil bearing formations can include up to three phases: primary, secondary and tertiary (or enhanced) recovery. During primary recovery, the natural energy present in the formation (e.g., water, gas) and/or gravity drives oil into the production wellbore. As oil is produced from an oil bearing formation, pressures and/or temperatures within the formation may decline. Artificial lift techniques (such as pumps) may be used to bring the oil to the surface. Only about 10 percent of a reservoir's original oil in place (OOIP) is typically produced during primary recovery. Secondary recovery techniques are employed to extend the field's productive life and generally include injecting a displacing fluid such as water (waterflooding) to displace oil and drive it to a production wellbore. Secondary recovery techniques typically result in the recovery of an additional 20 to 40 percent of a reservoir's OOIP. However, even if waterflooding were continued indefinitely, typically more than half of the OOIP would remain unrecovered due to a number of factors including, but not limited to, poor mixing efficiency between water and oil due to high interfacial tension between the water and oil, capillary forces in the formation, the temperature of the formation, the salinity of the water in the formation, the composition of the oil in the formation, and poor sweep of the injected water through the formation. Primary and secondary techniques therefore leave a significant amount of oil remaining in the reservoir.

With much of the easy-to-produce oil already recovered from oil fields, producers have employed tertiary, or enhanced oil recovery (EOR), techniques that offer potential for recovering 30 to 60 percent, or more, of a reservoir's OOIP. Three major categories of EOR have been found to be commercially successful. Thermal recovery EOR techniques involve the introduction of heat such as the injection of steam to lower the viscosity of the crude oil to improve its ability to flow through the reservoir. Gas injection EOR techniques use gases, such as nitrogen or carbon dioxide, that expand in a reservoir to push additional oil to a production wellbore, or other gases that dissolve in the oil to lower its viscosity and improve flowability of the oil. Chemical EOR techniques involve the injection of chemicals such as surfactants (surfactant flooding) to help lower the interfacial tension that prevents or inhibits oil droplets from moving through a reservoir, and polymers to allow the oil present in the formation to be more easily mobilized through the formation.

Chemical EOR techniques may be carried out prior to, during or after the implementation of primary and/or secondary recovery techniques. Chemical EOR techniques may also be carried out in conjunction with other EOR techniques that do not involve chemical injection. There are two main types of surfactant flooding techniques. Surfactant Polymer (SP) flooding involves injecting into a reservoir a fluid containing water and/or brine and about 1% by weight surfactant and about 0.1% by weight polymer. Alkali Surfactant Polymer (ASP) flooding involves the injection of water and/or brine containing alkali in addition to surfactant and polymer. ASP systems typically contain on the order of about 0.5-1 wt. % alkali, 0.1-1 wt. % surfactant and 0.1-1 wt. % polymer. Typically, an SP or ASP flood is followed up with an injection of a displacing fluid, e.g., a waterflood and/or polymer "push" fluid. The choice between SP or ASP depends on a number of factors, including the acid value of the oil to be recovered, the concentration of divalent ions ($Ca^{2+}$, $Mg^{2+}$) in the brine present in the reservoir, the economics of the project and the ability to carry out water softening or desalination. The surfactant component reduces interfacial tension between water and oil, while the polymer acts as a viscosity modifier and helps to mobilize the oil. Alkali sequesters divalent ions in the formation brine and thereby reduces the adsorption of the surfactant during displacement through the formation. Alkali also generates an anionic surfactant, sodium naphthenate soap, in situ in the formation by reacting with naphthenic acids that are naturally present in the crude oil. The use of relatively inexpensive alkali reduces the amount of surfactant required, and therefore the overall cost of the system. Alkali may also help alter formation wettability to a more water-wet state to improve the imbibition rate.

Introduction of surfactants into a reservoir, sometimes combined with altering the concentration of electrolytes therein, with the goal of displacing the sorbed oil by effecting spontaneous imbibition of water onto the reservoir rock, is an EOR technique known as "wettability alteration." This technique does not necessarily require low interfacial tensions between the oil and aqueous phases or the formation of a microemulsion phase. It also does not necessarily require a good sweep efficiency of the displacing fluid, and as such could have utility in carbonate reservoirs which can be fractured and typically have poor conformance. Surfactants used in SP and ASP floods have also displayed utility in wettability alteration based EOR techniques.

A surfactant EOR system, after injection into an oil bearing formation, takes up crude oil and brine from the formation to form a multiphase microemulsion in situ which when complete is immiscible with the reservoir crude and exhibits low interfacial tension (IFT) with the crude oil and brine. Commercial surfactant EOR processes are based on achieving ultra-low IFT (i.e., less than $10^{-2}$ mN/m) to mobilize disconnected crude oil droplets in the formation and create an oil bank where both oil and water flow as continuous phases. IFT changes with variables such as salinity, surfactant composition, crude oil composition and formation temperature. For anionic surfactants, an optimal salinity exists where microemulsions form which solubilize equal volumes of oil and water, and which exhibit nearly equal IFT's with oil and brine. The ultra-low IFT generally exists only in a narrow salinity range which overlaps the optimal salinity for a given microemulsion.

Internal olefin sulfonates (IOS) are anionic surfactants that have been evaluated as EOR surfactants. Internal olefin sulfonates may be prepared by sulfonation of internal olefins with the aid of $SO_3$ and inert gases and subsequent neutralization. Internal olefins may be subdivided as:

"di-substituted": R—CH=CH—R;
"tri-substituted": $R_2$C=CH—R;
and
"tetra-substituted": $R_2$C=C$R_2$; where R is straight or branched-chain hydrocarbyl.

Internal olefin sources can be obtained from a variety of processes, including olefin (e.g. ethylene, propylene and butylene) oligomerization processes, alpha-olefin metathesis processes, Fischer-Tropsch processes, catalytic dehydrogenation of long chain paraffin hydrocarbons, thermal cracking of hydrocarbon waxes and dimerized vinyl olefin processes. One well known ethylene oligomerization process is the Shell Higher Olefin Process (SHOP). This process combines ethylene oligomerization to form alpha-olefins, isomerization of the alpha-olefins to form internal olefins and the metathesis of these internal olefins with butenes or ethylene to form alpha-olefins of different chain lengths. A problem associated with SHOP mentioned in U.S. Pat. No. 6,777,584 is undesirable branching on the alpha-olefins and internal olefins that often result from the oligomerization/isomerization/metathesis processes. Commercially available internal olefins typically contain on the order of about six mole percent or higher of tri-substituted internal olefins. Moreover, these commercial products typically contain appreciable amounts of non-linear, alkyl branched products. These alpha-olefins and internal olefins have been reported to contain alkyl branching on the order of about six mole percent or higher. Moreover, significant amounts of unreactive, terminally unsaturated vinylidenes of the structure $R_2C=CH_2$ (where R is defined as above) are also known to be present in these commercially available materials.

U.S. Pat. Nos. 4,532,053, 4,549,607, 4,555,351, 4,556,108, 4,597,879, 4,733,728 and 4,765,408, disclose micellar slugs containing among other things an internal olefin sulfonate for use in the recovery of oil.

SUMMARY OF THE INVENTION

It has now been found that sulfonates of internal olefins containing minimal amounts of tri-substituted internal olefins possess unique performance advantages in EOR applications over sulfonates of internal olefins containing appreciable amounts, i.e., greater than about six mole percent, of tri-substituted internal olefins. More particularly, it has been discovered that optimal salinities of microemulsions made from internal olefins containing low amounts of tri-substituted internal olefins are significantly lower than optimal salinities of microemulsions made from internal olefins of the same carbon chain length that contain appreciable amounts of tri-substituted internal olefins. Lower optimal salinities imply increased utility in formulations for use in the enhanced recovery of, among other things, waxy crude oils.

Therefore, in a first aspect of the disclosure there is provided a process for recovering oil from an oil-bearing formation which comprises introducing into said formation an aqueous composition comprising at least one sulfonated derivative of an internal olefin or mixture of internal olefins wherein said internal olefin or mixture of internal olefins corresponds to the formula (I):

$$R^1R^2C=CR^3R^4 \quad \quad (I)$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44, with the proviso that at least about 96 mole percent of $R^1$ and $R^3$ are straight- or branched-chain, saturated hydrocarbyl groups and at least about 96 mole percent of $R^2$ and $R^4$ are hydrogen in the internal olefin or mixture of internal olefins. The internal olefins of the formula $R^1R^2C=CR^3R^4$ may be obtained via the metathesis of a feedstock comprising alpha-olefin or mixture of alpha-olefins of the formula $R^5HC=CH_2$ wherein $R^5$ is a straight- or branched-chain $C_3$-$C_{22}$ hydrocarbyl group. The metathesis reaction is one which is highly selective to the formation of di-substituted internal olefins of the formula $R^1R^2C=CR^3R^4$ wherein at least about 96, preferably at least about 97, more preferably at least about 98, and most preferably at least about 99, mole percent of $R^1$ and $R^3$ are straight- or branched-chain, saturated hydrocarbyl groups and at least about 96, preferably at least about 97, more preferably at least about 98, and most preferably at least about 99, mole percent of $R^2$ and $R^4$ are hydrogen. In an embodiment of this first aspect of the disclosure, the $R^1$ and $R^3$ straight- or branched-chain, saturated hydrocarbyl groups possess low amounts, i.e., on the order of less than about 6 mole %, of alkyl branching. The metathesis reaction may be conducted in the presence of metathesis catalyst. Suitable metathesis catalysts include, but are not limited to, Grubbs, Hoveyda-Grubbs and Schrock catalysts.

In a second aspect of the disclosure there is provided a composition for use in the recovery of oil from an oil-bearing formation, the composition comprising:
(i) water;
(ii) at least one sulfonated derivative of an internal olefin or mixture of internal olefins wherein said internal olefin or mixture of internal olefins corresponds to the formula (I):

$$R^1R^2C=CR^3R^4 \quad \quad (I)$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44, with the proviso that at least about 96 mole percent of $R^1$ and $R^3$ are straight- or branched-chain, saturated hydrocarbyl groups and at least about 96 mole percent of $R^2$ and $R^4$ are hydrogen in the internal olefin or mixture of internal olefins; and
(iii) optionally one or more additional components.
In one embodiment of this second aspect of the disclosure, additional components including, but not limited to, co-surfactants, solvents, polymers, alkali, and various combinations thereof, may be employed.

In a third aspect of the disclosure there is provided a process for recovering oil from an oil-bearing formation which comprises introducing into said formation an aqueous composition comprising at least one sulfonated derivative of an internal olefin or mixture of internal olefins wherein said internal olefin or mixture of internal olefins is obtained via the metathesis of an alpha-olefin or mixture of alpha-olefins in the presence of a metathesis catalyst comprising a Group 8 transition metal complex.

In a fourth aspect of the present disclosure there is provided a composition for use in the recovery of oil from an oil-bearing formation, the composition comprising:
(i) water;
(ii) at least one sulfonated derivative of an internal olefin or mixture of internal olefins wherein said internal olefin or mixture of internal olefins is obtained via the metathesis of an alpha-olefin or mixture of alpha-olefins in the presence of a metathesis catalyst comprising a Group 8 transition metal complex; and
(iii) optionally one or more additional components. In one embodiment of this fourth aspect of the disclosure, additional components including, but not limited to, co-surfactants, solvents, polymers, alkali, and various combinations thereof, may be employed.

In accordance with a fifth aspect of the disclosure there is provided a sulfonated derivative of an internal olefin or mixture of internal olefins wherein said internal olefin or mixture of internal olefins corresponds to the formula (I):

$$R^1R^2C=CR^3R^4 \quad \quad (I)$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44, with the proviso that at least about 96 mole percent of $R^1$ and $R^3$ are straight- or branched-chain, saturated hydrocarbyl groups and at least about 96 mole percent of $R^2$ and $R^4$ are hydrogen in the internal olefin or mixture of internal olefins.

In accordance with a sixth aspect of the disclosure there is provided a sulfonated derivative of an internal olefin or mixture of internal olefins wherein said internal olefin or mixture of internal olefins is obtained via the metathesis of an alpha-olefin or mixture of alpha-olefins in the presence of a metathesis catalyst comprising a Group 8 transition metal complex.

It has been discovered that sulfonated derivatives of internal olefins or mixtures of internal olefins possessing low amounts of tri-substitution on the double bond, i.e., less than about 4 mole percent tri-substitution, offer unique and significant performance advantages in a surfactant EOR system. Sulfonated derivatives of internal olefins containing low amounts of tri-substitution as disclosed herein display lower optimal salinities than sulfonated derivatives of internal olefins having the same carbon chain lengths but possessing significant amounts of tri-substituted internal olefins. The sulfonated derivatives of internal olefins described herein may offer a route to the enhanced recovery of, among other things, waxy crude oils.

It has also been discovered that sulfonated derivatives of internal olefins or mixtures of internal olefins, wherein the internal olefins are made by the metathesis of an alpha-olefin or mixture of alpha-olefins in the presence of a metathesis catalyst comprising a Group 8 transition metal complex, may be advantageously employed as EOR surfactants. The Group 8 transitional metal complex is more fully described hereinbelow.

The mole % 1,2-di-substituted olefin is defined as the quotient of one half the integrated intensity of region B divided by the sum of one half the integrated intensity of region B and the integrated intensity of region C multiplied by 100. The mole % 1,2-di-substituted olefin in region B is 79.7% (i.e., 100×(91.95/2)/((91.95/2)+11.69)). This IO was used to make C-IOS-1, C-IOS-2, and C-IOS-11.

Figure 1:
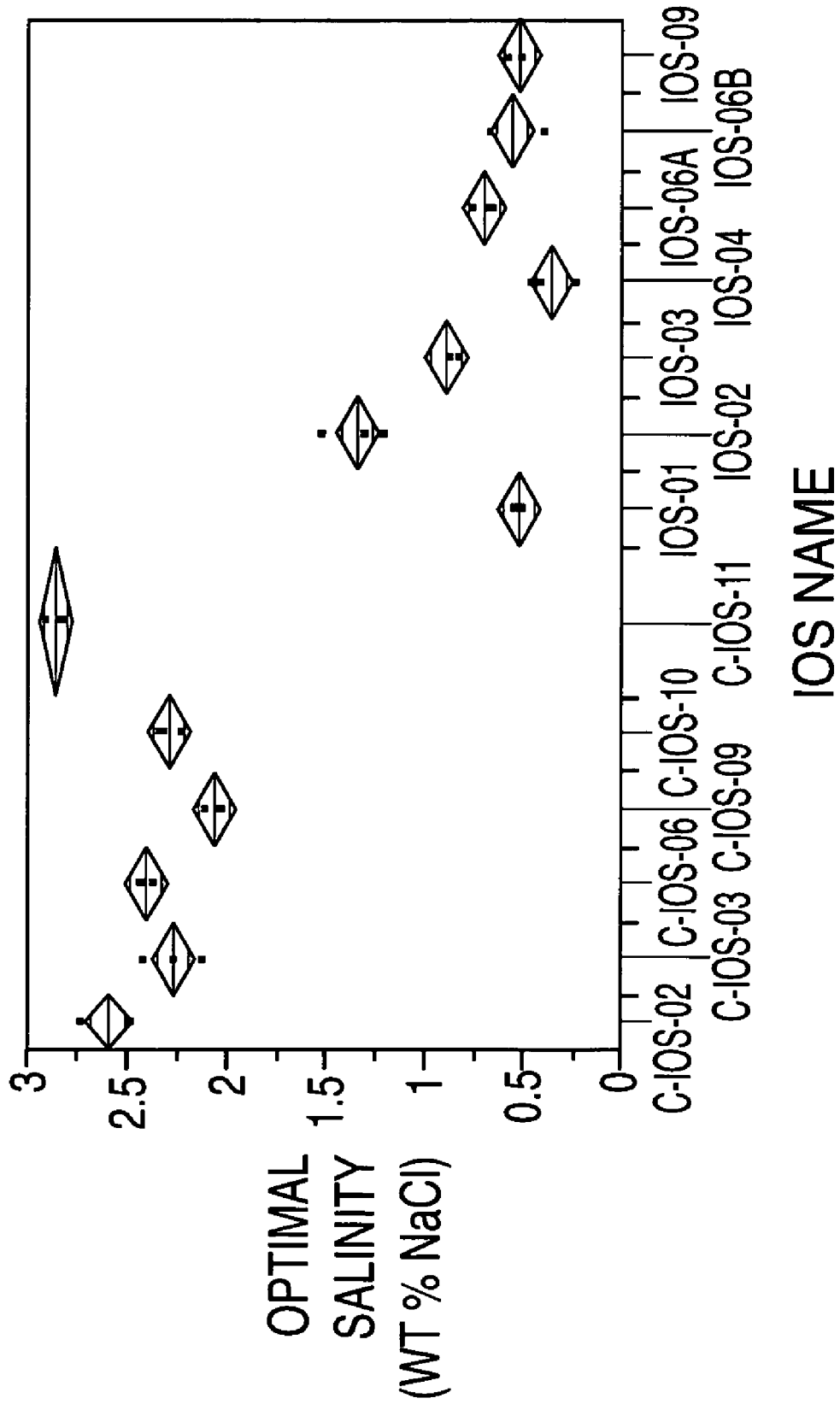
FIG. 1 depicts optimal salinities for single component formulations (2 wt. % IOS; 4 wt. % Butylcellosolve®) of various IOS compositions against decane at 50° C. by IOS name. The diamonds encompass the upper and lower 95% confidence levels of the optimal salinity averages.
Figure 2:
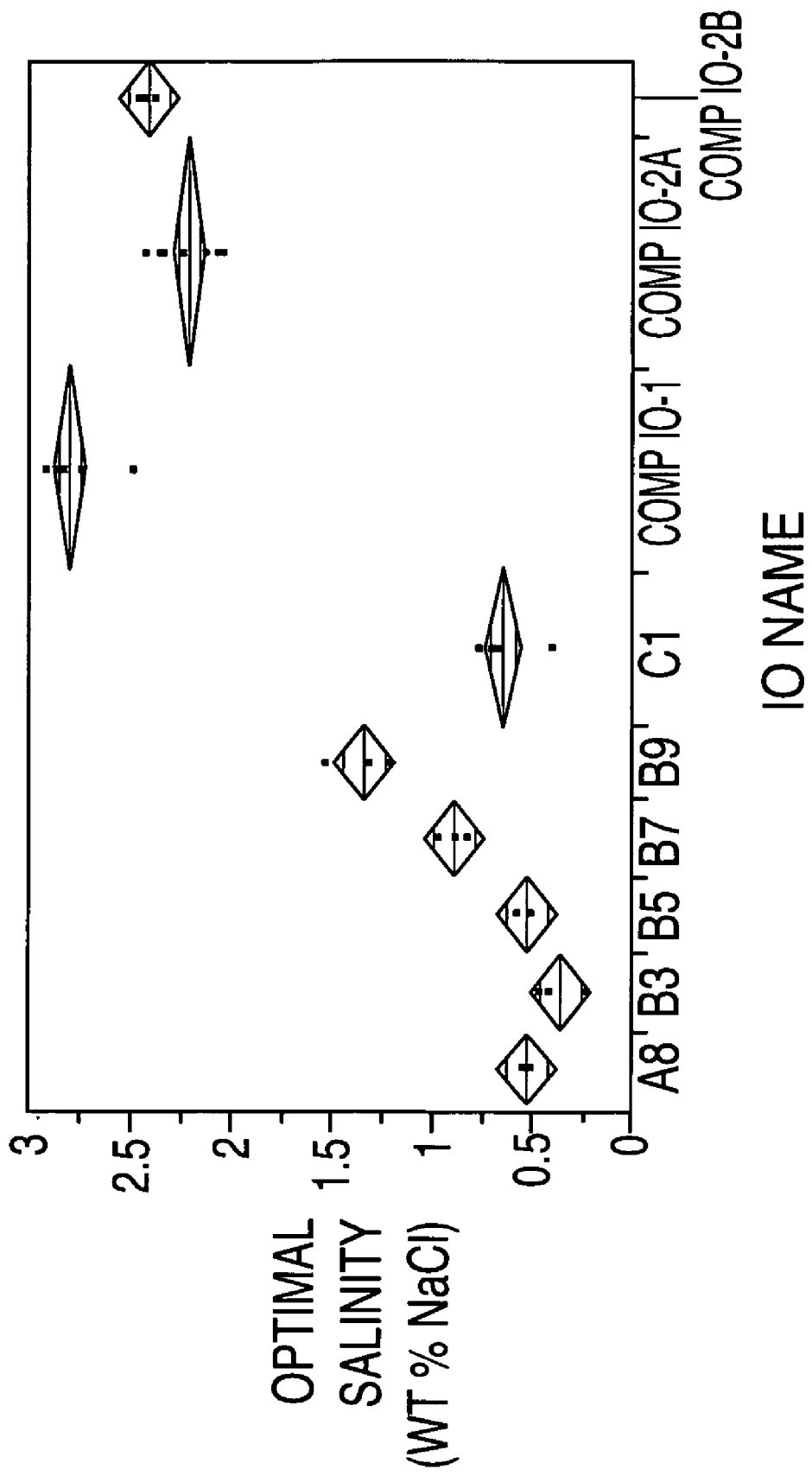
FIG. 2 depicts optimal salinities for single component formulations (2 wt. % IOS; 4 wt. % Butylcellosolve) of various IOS compositions against decane at 50° C. by IO name. The diamonds encompass the upper and lower 95% confidence levels of the optimal salinity averages formulations.
Figure 3:
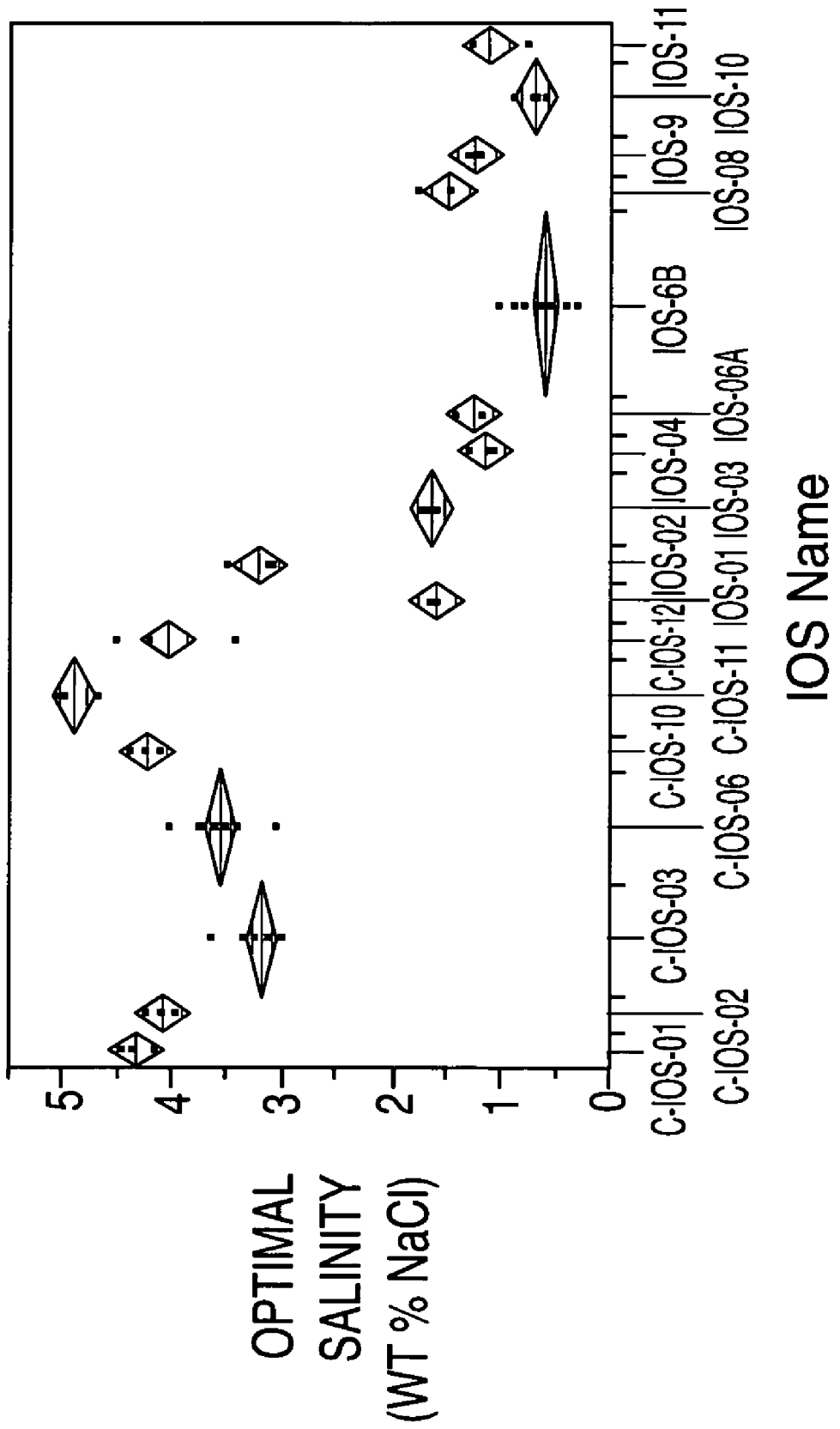
FIG. 3 depicts optimal salinities for dual component formulations (2 wt. % of 80:20 IOS: branched sodium dodecylbenzene sulfonate, sodium salt; 4 wt. % Butylcellosolve; 1 wt. % $Na_2CO_3$) of various IOS compositions against dodecane at 50° C. by IOS name. The diamonds encompass the upper and lower 95% confidence levels of the optimal salinity averages.
Figure 4:
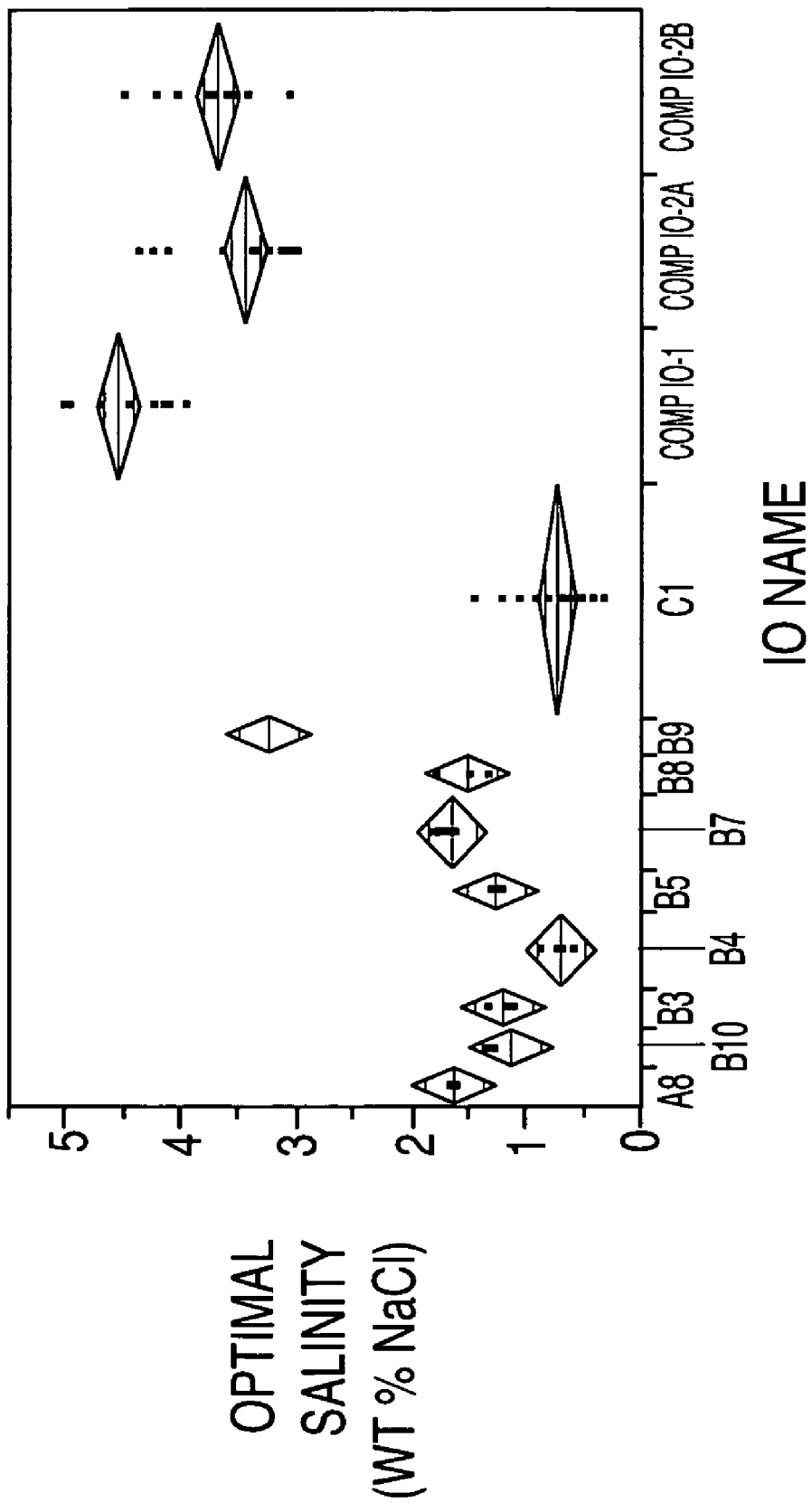
FIG. 4 depicts optimal salinities for dual component formulations (2 wt. % of 80:20 IOS: branched sodium dodecylbenzene sulfonate, sodium salt; 4 wt. % Butylcellosolve; 1 wt. % $Na_2CO_3$) of various IOS compositions against dodecane at 50° C. by IO name. The diamonds encompass the upper and lower 95% confidence levels of the optimal salinity averages.
Figure 5:
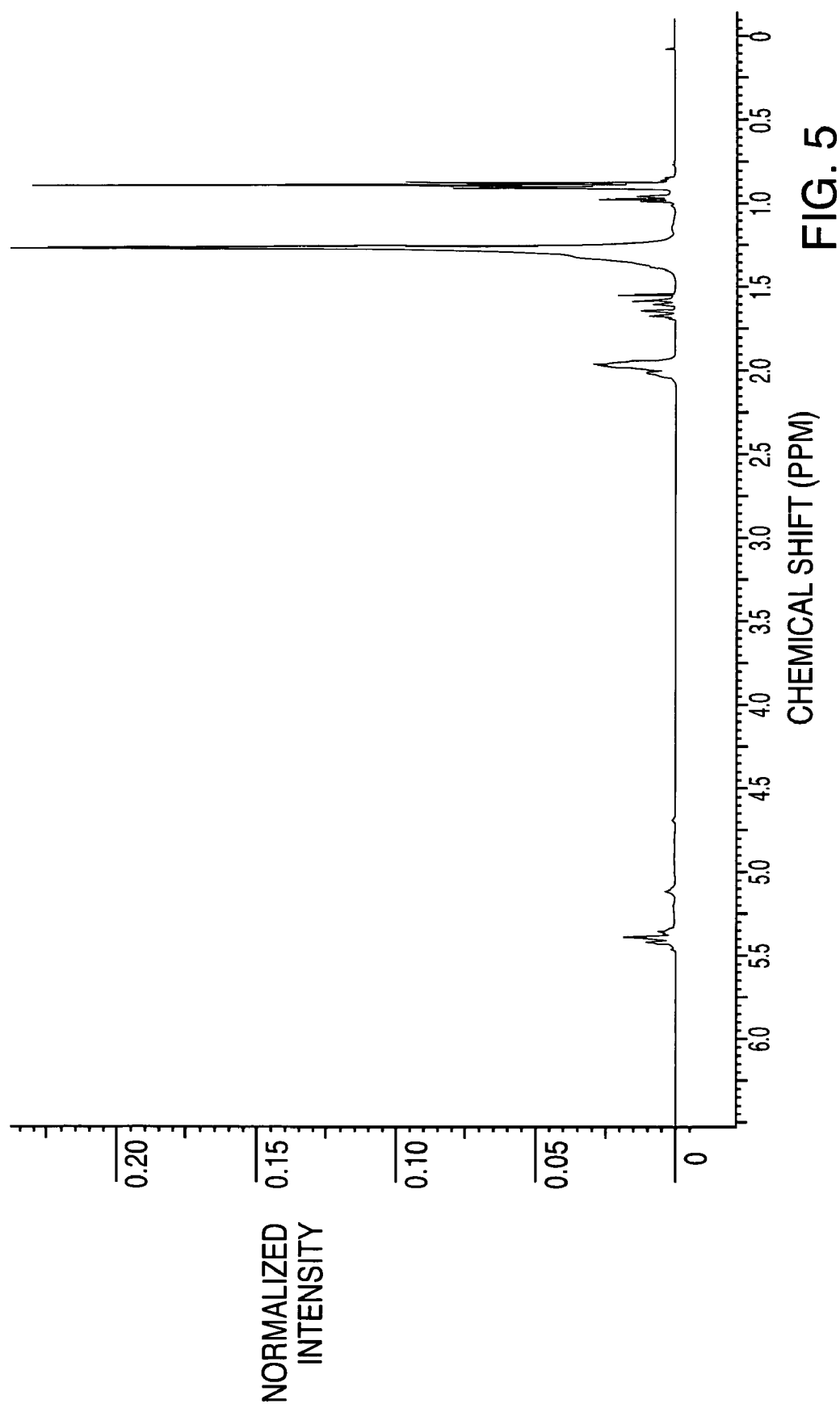
FIG. 5 depicts the $^1$HNMR spectrum of Comp IO-1. Features associated with unsaturation in this material are found between about 4.5 and 6.0 ppm.
Figure 6A:
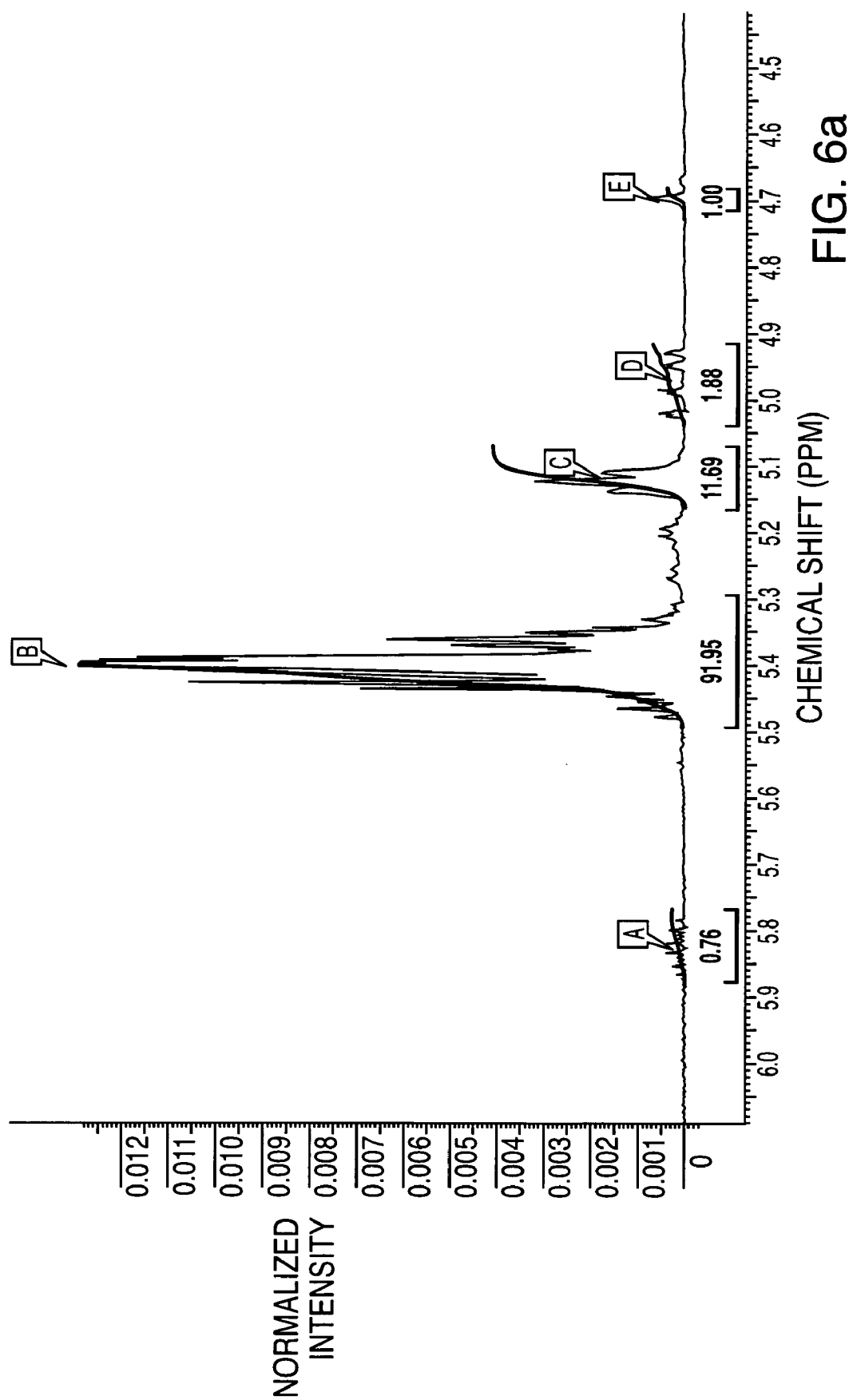
FIG. 6a depicts a detail of the $^1$HNMR spectrum of FIG. 5. Regions A and D are associated with residual alpha-olefin; region E is associated with vinylidene components (i.e., 1,1-di-substituted olefins). Regions B and C are associated with 1,2-di- and 1,2,3-tri-substituted internal olefins, respectively.
Figure 6B:
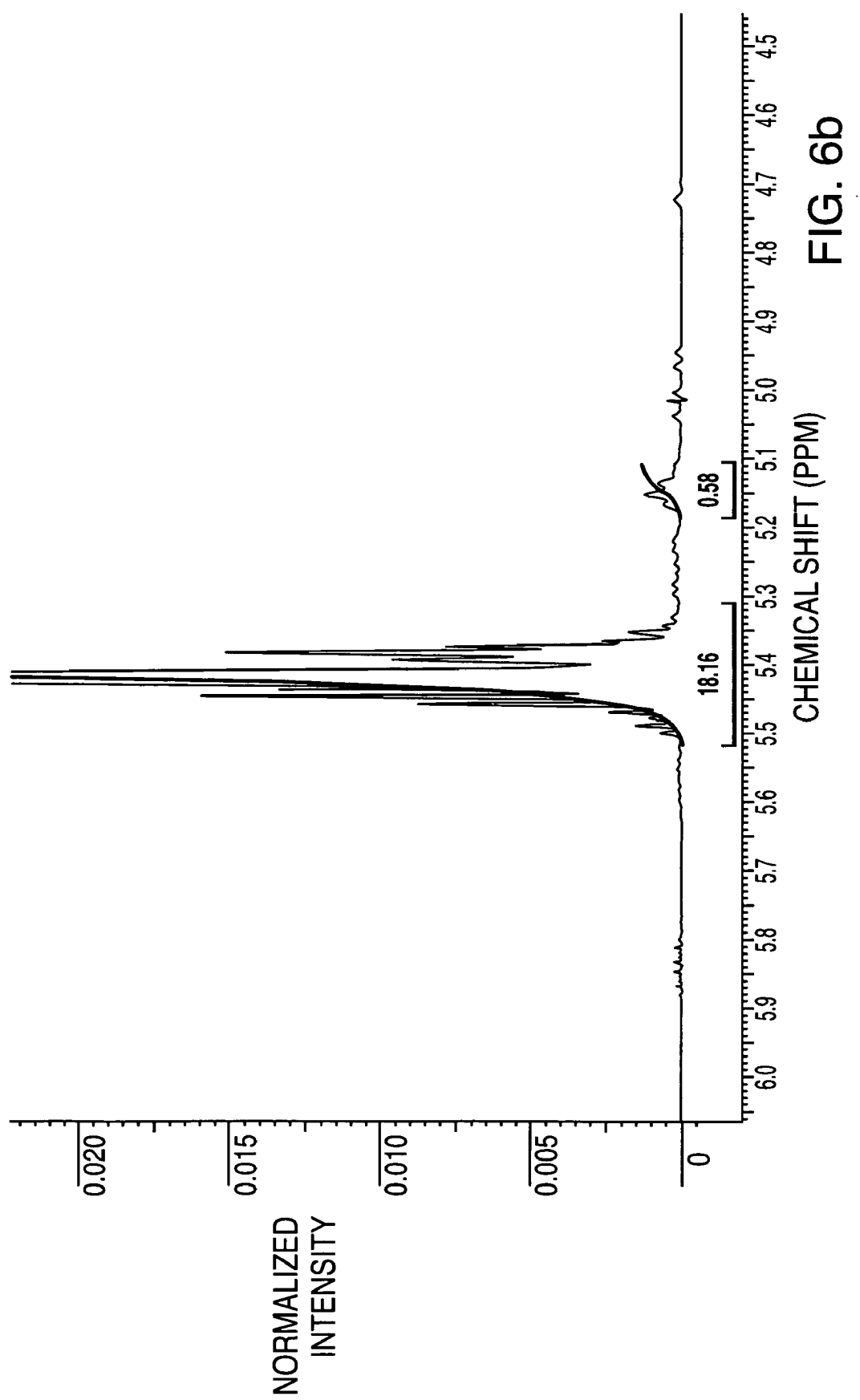

FIG. 6b depicts the $^1$HNMR spectrum of Comp IO-2A, used to make C-IOS-3, C-IOS-9, and C-IOS-10. The mole % 1,2-di-substituted olefin is 94.0 mole %.

Figure 6C:
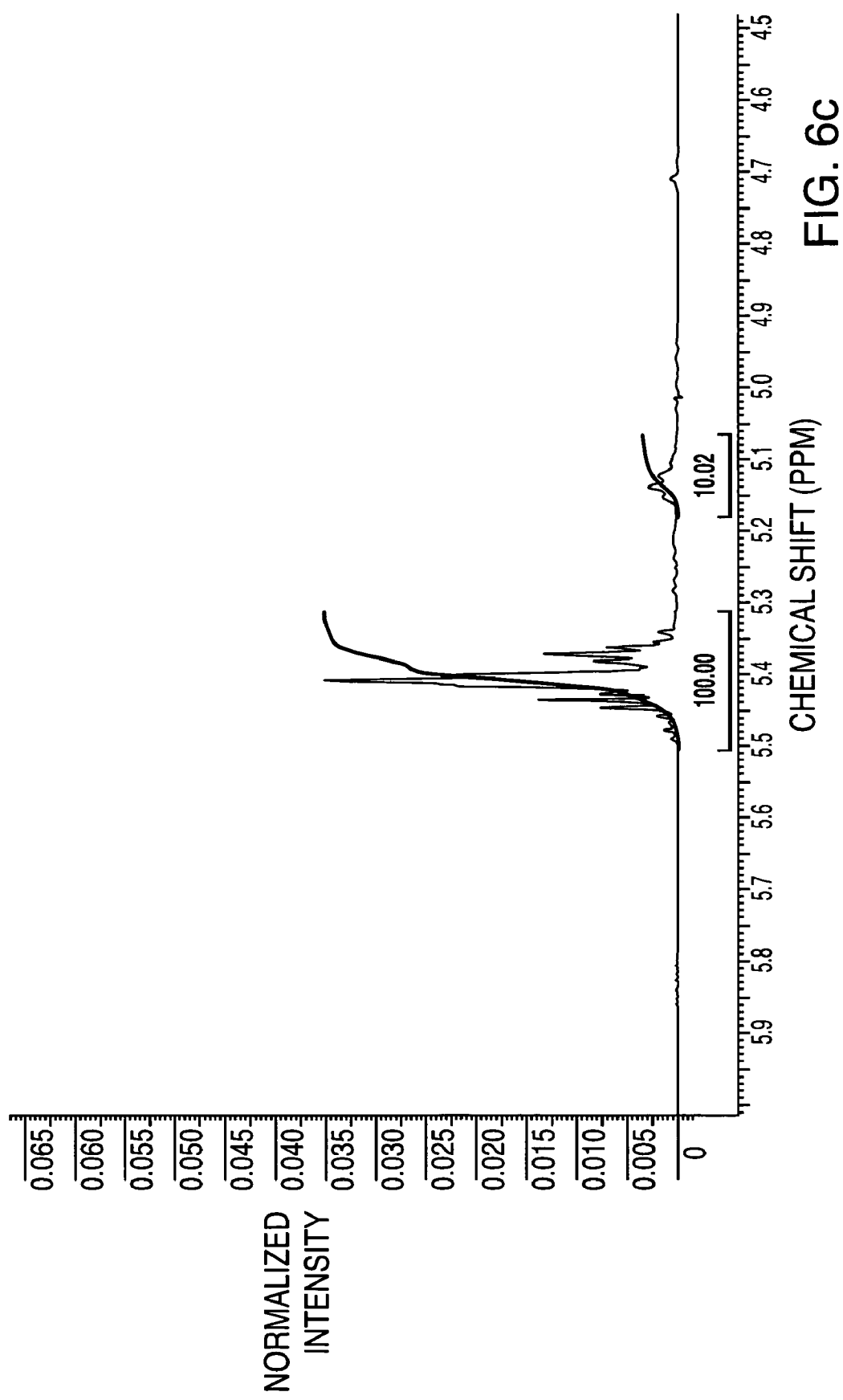

FIG. 6c depicts the $^1$HNMR spectrum of Comp IO-2B used to make C-IOS-6 and C-IOS-12. The mole % 1,2-di-substituted olefin is 90.9 mole %.

Figure 6D:
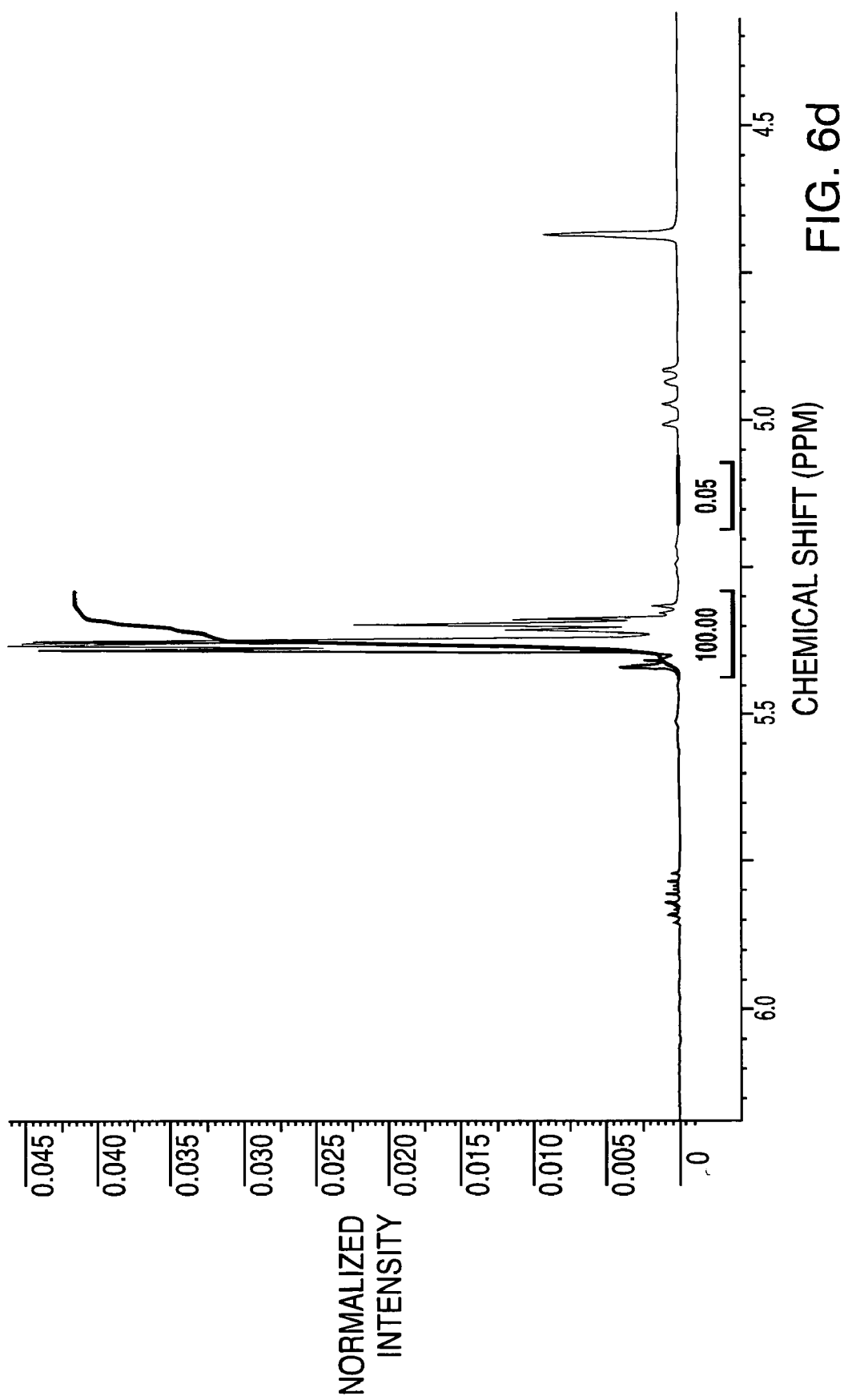

FIG. 6d depicts the $^1$HNMR spectrum of internal olefin B3 used to make IOS-4. The mole % 1,2-di-substituted olefin is greater than 99.9%.

Figure 7:
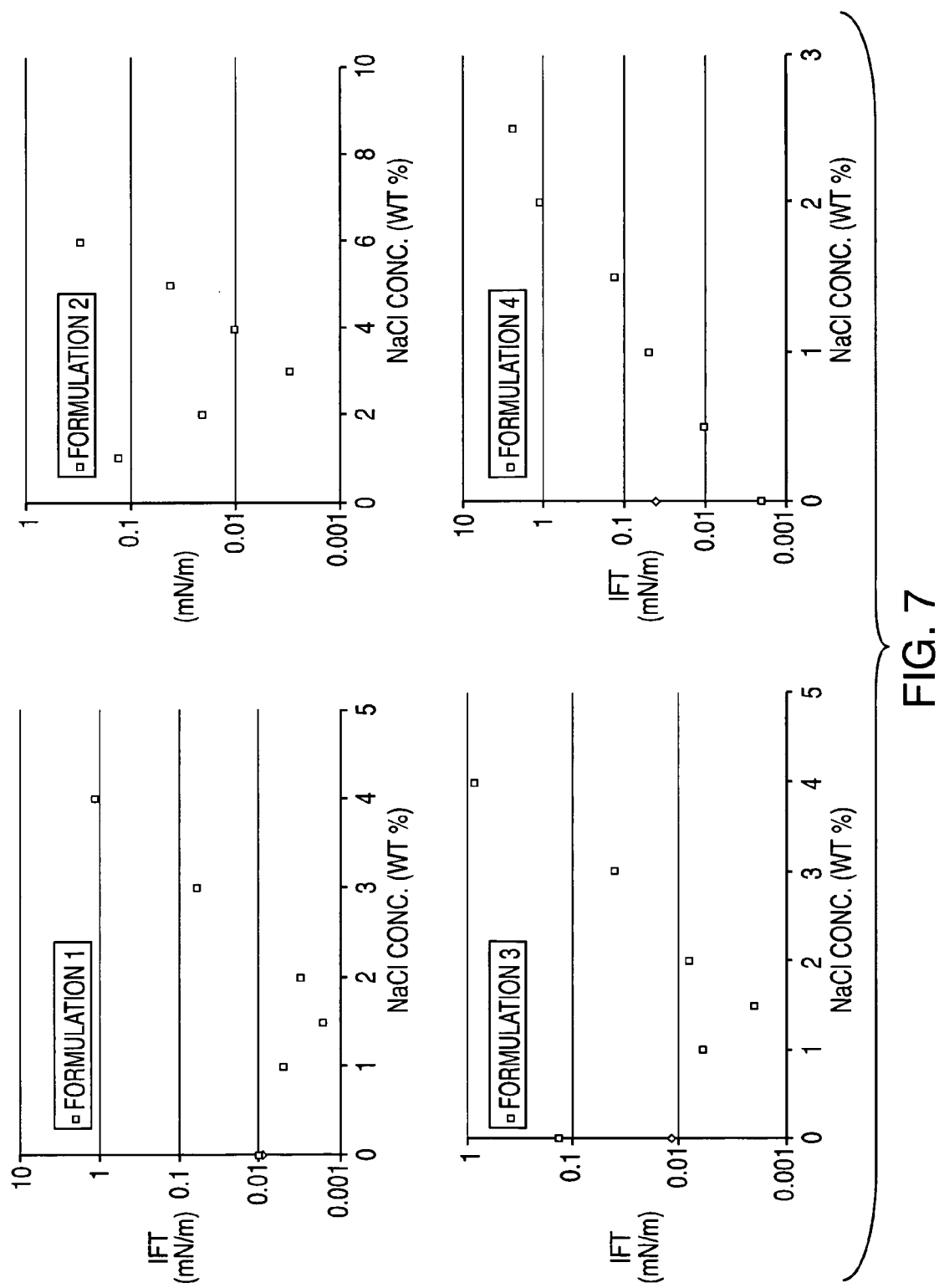

FIG. 7 graphically depicts the interfacial tension (IFT) measurements of various EOR formulations against various crude Formulations 1-4 against oils at different salinities.

Figure 8:
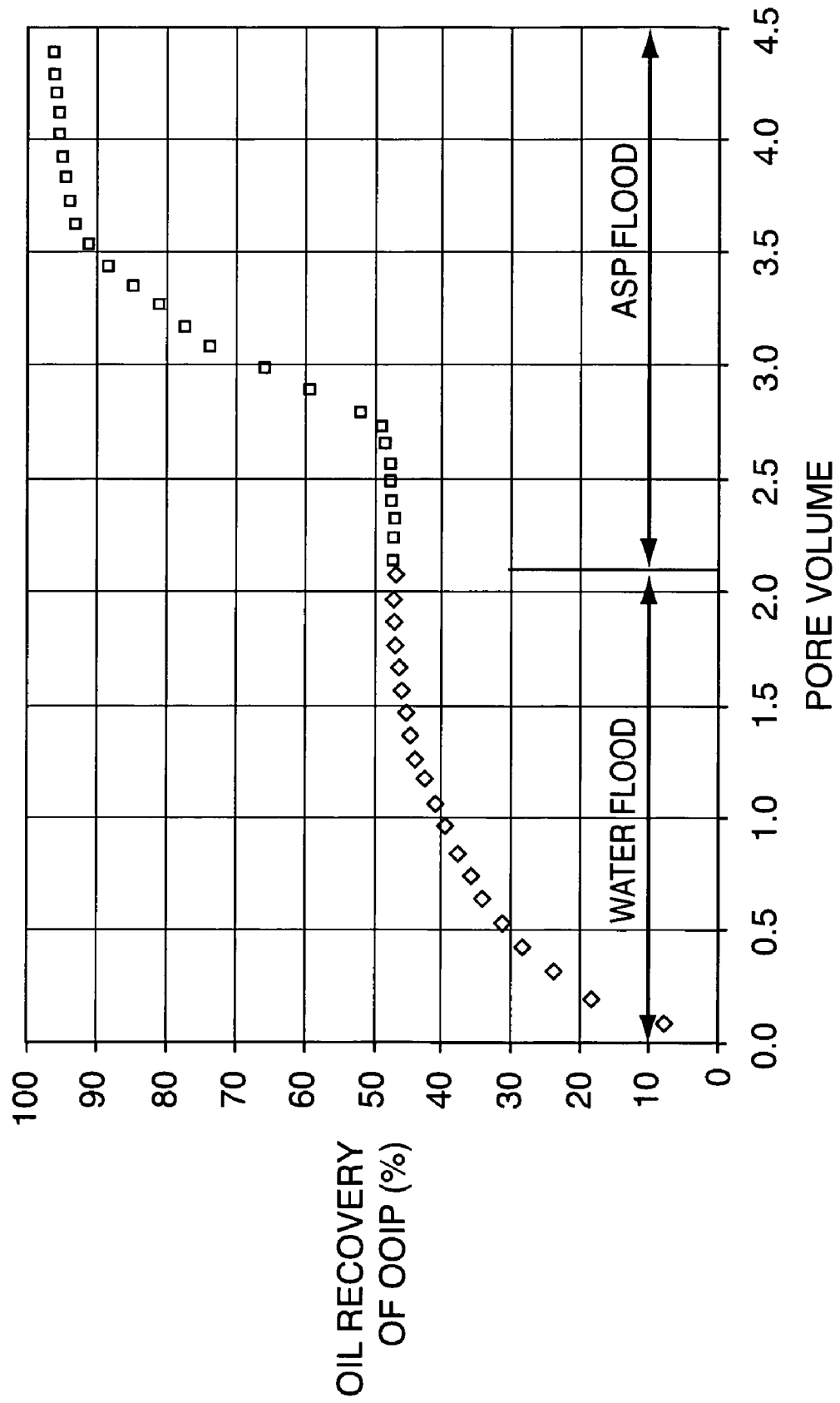

FIG. 8 graphically depicts the oil recovery of original oil in place (OOIP) (%) for both waterflood and alkali surfactant polymer (ASP) flood using phases of the core-flood experiment.

Figure 9:
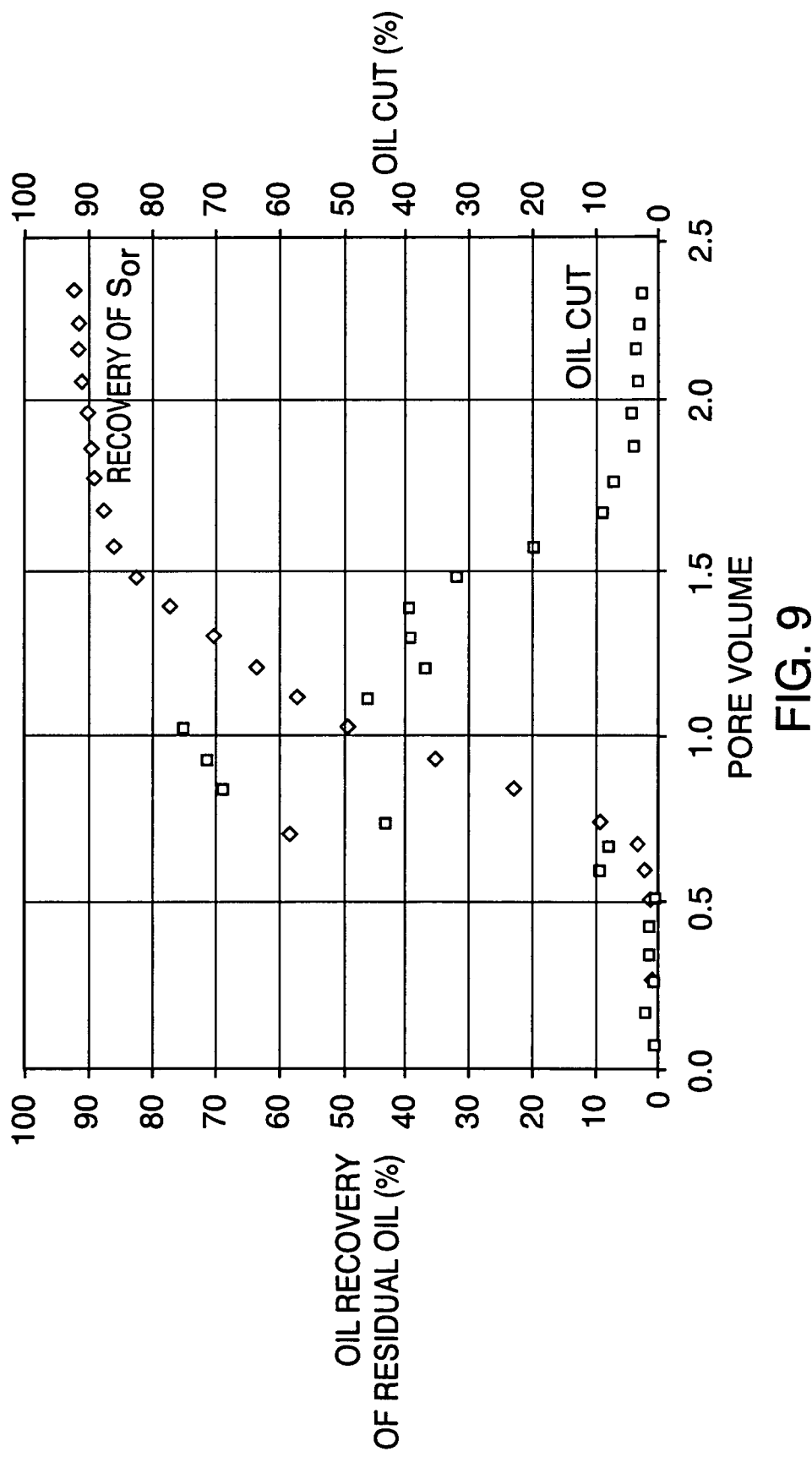

FIG. 9 graphically depicts the oil recovery of residue oil (%) for the ASP phase of the core flood experiment.

Figure 10:
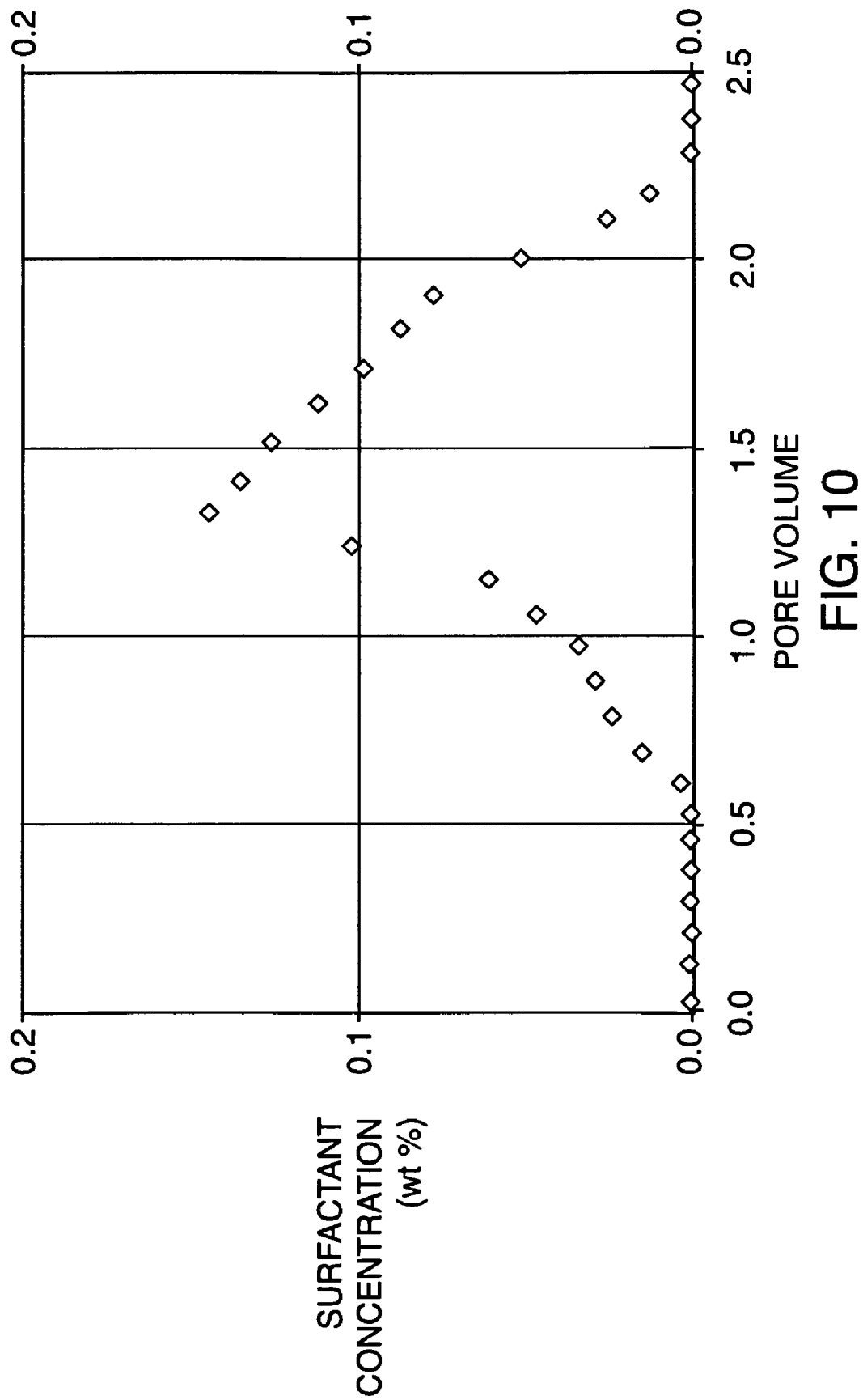

FIG. 10 graphically depicts the surfactant concentration in the effluent for the core flood experiment.

Figure 11:
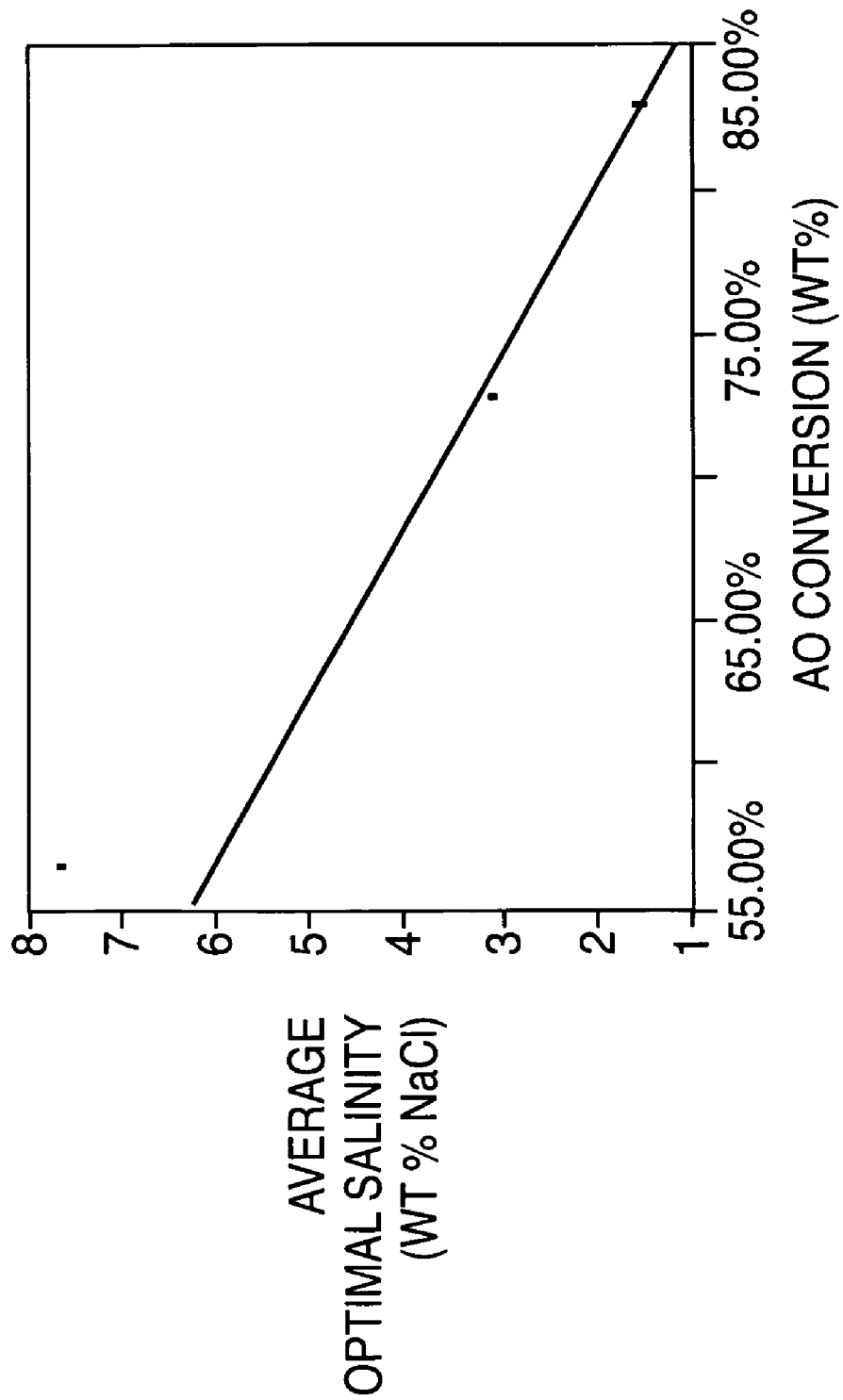

FIG. 11 graphically depicts the effect of alpha-olefin (AO) conversion on optimal salinity for a Single Component Formulation. This figure plots optimal salinity against decane at 50° C. as a function of alpha-olefin conversion. The surfactant formulation is 2 wt. % IOS, 4 wt. % Butylcellosolve. The $R^2$ of the linear fit is 0.9621.

Figure 12:
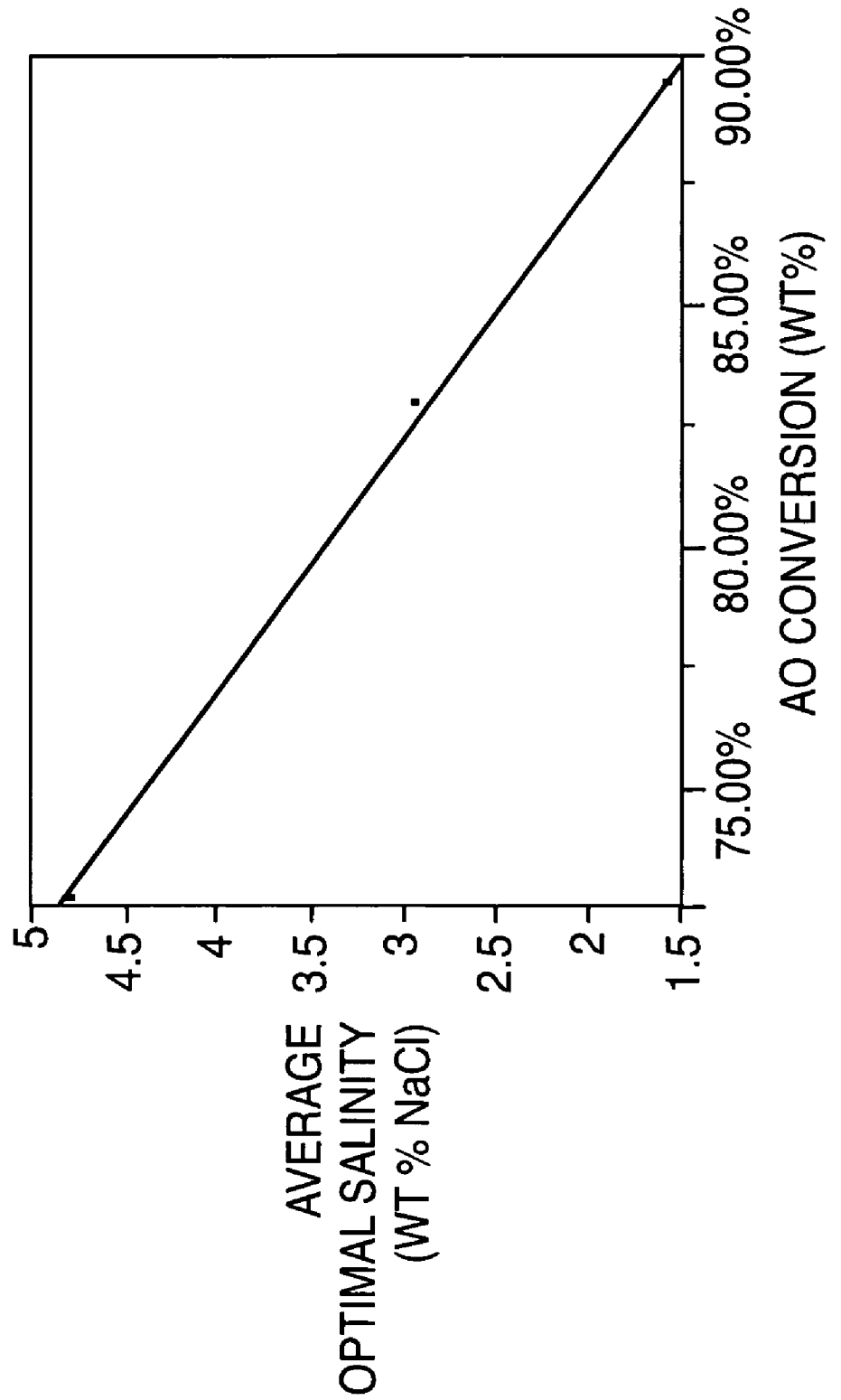

FIG. 12 graphically depicts the effect of alpha-olefin conversion on optimal salinity for a Dual Component Formulation. This figure plots optimal salinity against dodecane at 50° C. as a function of alpha-olefin conversion. The surfactant formulation is 80:20::IOS:Petrostep® C-8 by weight (2 wt. % total surfactant), 4 wt. % Butylcellosolve, 1 wt. % sodium carbonate. The $R^2$ of the linear fit is 0.9992.

DESCRIPTION OF THE PREFERRED EMBODIMENTS

Definitions

As used herein, the following terms have the following meanings unless expressly stated to the contrary:

The term "co-surfactant" herein refers to anionic, nonionic, zwitterionic, amphoteric or cationic surfactants that may be used in conjunction with the sulfonated derivatives of internal olefins described herein in enhanced oil recovery compositions and processes. The use of co-surfactants may impart higher tolerance to polyvalent ions, and widen the range of low and stable interfacial tensions between brine and crude oil. They may also provide a reduction in viscosity of the sulfonated internal olefin surfactants disclosed herein.

The term "crude oil" as used herein refers to hydrocarbons formed primarily of carbon and hydrogen atoms. The hydrocarbons may also include other elements, such as, but not limited to, halogens, metallic elements, nitrogen, oxygen and/or sulfur. Hydrocarbons derived from an oil-bearing formation may include, but are not limited to, kerogen, bitumen, pyrobitumen, asphaltenes, resins, oils or combinations thereof.

The terms "enhanced oil recovery" or "EOR" as used herein refer to processes for enhancing the recovery of hydrocarbons from subterranean reservoirs by the introduction of materials not naturally occurring in the reservoir.

The terms "interfacial tension" or "IFT" as used herein refer to the tension between oil and water of different salinities. To achieve high enhanced oil recovery, it is often necessary to reduce the interfacial tension between the oil and the water in the reservoir to less than about 0.01 mN/m. Interfacial tensions may be measured using a spinning drop tensiometer or by making observations of phase behavior according to the methods described in Levitt, D. B.; Jackson, A. C.; Heinson, C.; Britton, L. N.; Malik, T.; Dwarakanath, V.; Pope, G. A., Identification and Evaluation of High Performance EOR Surfactants. *SPE* 2006, (100089), 1-11, Levitt, D. B. Experimental Evaluation of High Performance EOR Surfactants for a Dolomite Oil Reservoir. University of Texas, Austin, 2006, Zhao, P.; Jackson, A. C.; Britton, C.; Kim, D. H.; Britton, L. N.; Levitt, D. B., Development of High-Performance Surfactants for Difficult Oils. *SPE* 2008, (113432). Interfacial tension may be also measured by any known method for measuring interfacial tension.

The term "microemulsion" as used herein refers to a thermodynamically stable, micellar dispersion of oil, brine, the sulfonated internal olefin surfactant described herein and optionally one or more additional components. Microemulsions are defined as those emulsions having an average particle size of less than about one hundred nanometers. Mixtures of water, oil, salt, surfactants, and other components mentioned above may be described as exhibiting Winsor type I, II or III behavior. Winsor type I systems are those that may be distinguished by oil solubilized in the aqueous phase; Winsor type II systems are those that may be distinguished by water solubilized in the oil phase. Winsor type III systems are microemulsions that may coexist with both excess oil and excess brine phases. A transition in phase behavior from type I to type III to type II systems is known to be caused by changing a variable such as salinity, temperature, surfactant or oil composition. It is generally known and widely accepted that microemulsions in which approximately equal volumes of oil and aqueous components are solubilized provide the lowest IFT's.

The term "oil-bearing formation" as used herein refers to subterranean reservoirs composed of one or more hydrocarbon-containing layers, one or more non-hydrocarbon layers, an overburden and/or an underburden. An "overburden" and/or an "underburden" may include one or more different types of impermeable materials. For example, overburden/underburden may include rock, shale, mudstone, or wet/tight carbonate (i.e., an impermeable carbonate without hydrocarbons). For example, an underburden may contain shale or mudstone. In some cases, the overburden/underburden may be somewhat permeable. For example, an underburden may be composed of a permeable mineral such as sandstone or limestone. Properties of a hydrocarbon-containing formation may affect how hydrocarbons flow through an underburden/overburden to one or more production wells. Properties may include, but are not limited to, porosity, permeability, pore size distribution, surface area, salinity or temperature of formation. Overburden/underburden properties in combination with hydrocarbon properties, such as, capillary pressure (static) characteristics and relative permeability (flow) characteristics may effect mobilization of hydrocarbons through the oil-bearing formation.

The term "optimal salinity" as used herein refers to the salinity at which substantially equal amounts by volume of oil and brine are solubilized in the microemulsion and the interfacial tension between the microemulsion and the excess brine phase substantially equals the interfacial tension between the microemulsion and the excess oil phase.

The term "waxy crude oil" as used herein refers to crude oil having an API value of less than 22.3° and usually containing a variety of light and intermediate hydrocarbons, such as paraffins and aromatic hydrocarbons, wax paraffins and a variety of other heavy organic compounds, such as resins and asphaltenes.

Alpha-Olefin Feedstock

Alpha-olefin feedstocks that may be advantageously employed in the practice of the disclosure are alpha-olefins corresponding to the formula $R^5HC\!=\!CH_2$, wherein $R^5$ is a straight- or branched-chain saturated $C_3$-$C_{22}$ hydrocarbyl group. While the $R^5$ group may contain some amount of alkyl branching depending on the process used to make the alpha-olefin feedstock, $R^5$ groups possessing low amounts of alkyl branching, i.e., on the order of less than about 6, preferably less than about 3, more preferably less than about 2, most preferably less than about 1, mole % alkyl branching, are particularly advantageous in the practice of the present disclosure. In a presently preferred embodiment of the disclosure, the alpha-olefin feedstock comprises an alpha-olefin corresponding to the formula $R^5HC\!=\!CH_2$ in which $R^5$ is a $C_8$, $C_9$, $C_{10}$, $C_{11}$, or $C_{12}$ hydrocarbyl group, more preferably a $C_8$, $C_{10}$ or $C_{12}$ hydrocarbyl group, or a mixture of two or more different alpha-olefins in which $R^5$ is a $C_8$, $C_9$, $C_{10}$, $C_{11}$, or $C_{12}$ hydrocarbyl group, more preferably a $C_8$, $C_{10}$ or $C_{12}$ hydrocarbyl group. In accordance with this preferred embodiment, small amounts, i.e., combined amounts of less than about five weight percent, of $<C_8$ and $>C_{12}R^5$ hydrocarbyl groups may be present in the alpha-olefin feedstock. Non-limiting examples of alpha-olefin feedstocks which are useful in the practice of the disclosure may contain the following:

| Hydrocarbon Type | Mole % | Preferred Mole % |
|---|---|---|
| $C_{10}$-$C_{14}$ linear alpha-olefins | >90 | >95 |
| $<C_{10}$ and $>C_{14}$ linear alpha-olefins | <5 | <3 |
| Vinylidenes | <6 | <4 |
| Branched alpha-olefins | <6 | <3 |
| Internal olefins | <5 | <0.4 |
| Paraffins | <0.4 | <0.2 |

The alpha-olefins may be derived from oligomerizing ethylene in the presence of either organoaluminum compounds, transition metal catalysts or acidic zeolites to produce a wide range of chain lengths that are further purified by various known means, preferably distillation. See, e.g., U.S. Pat. Nos. 3,647,906, 4,727,203, and 4,895,997 to Shell Oil Co., U.S. Pat. No. 5,849,974 to Amoco Corp., and U.S. Pat. No. 6,281,404 to Chevron Chemicals, each being incorporated by reference herein for their disclosures of suitable catalysts and processing conditions for ethylene oligomerization. Such alpha-olefin feedstocks are commercially available from a variety of sources, including Shell Chemicals, Exxon Chemicals, Ineos and Chevron Phillips Chemical Company.

Metathesis Products

In an embodiment of the disclosure, the above-described alpha-olefin feedstock, optionally in combination with one or more additional unsaturated compounds, is subjected to metathesis reaction conditions in the presence of a suitable metathesis catalyst, particularly one comprising a Group 8 transition metal complex. The metathesis reaction may be used to produce suitable long chain internal olefins that may be subsequently sulfonated to produce a sulfonated derivative that may be advantageously employed in enhanced oil recovery compositions.

The above-described metathesis reaction may result in the production of an internal olefin or mixture of internal olefins wherein said internal olefin or mixture of internal olefins corresponds to the formula (I):

$$R^1R^2C\!\!=\!\!CR^3R^4 \quad (I)$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44, with the proviso that at least about 96 mole percent of $R^1$ and $R^3$ are straight- or branched-chain, saturated hydrocarbyl groups and at least about 96 mole percent of $R^2$ and $R^4$ are hydrogen in the internal olefin or mixture of internal olefins.

The reaction product resulting from the above described metathesis reaction may itself constitute a mixture containing the internal olefins or mixture of internal olefins as described herein in combination with components other than the internal olefin or mixture of internal olefins. Examples of such components besides internal olefins that may be found in such mixtures include alpha-olefins and vinylidenes. Where the metathesis reaction does not proceed to completion, the reaction product may contain appreciable amounts of alpha-olefin. Such reaction products containing mixtures of internal olefins in combination with other components may be subjected to sulfonation conditions to produce compositions that may advantageously be employed in enhanced oil recovery compositions without the need to remove any components that are not internal olefins from either the mixtures themselves or from the products resulting from the sulfonation of these mixtures. If desired, such components may be removed from the mixtures or products resulting from the sulfonation of these mixtures by any removal technique known to those skilled in the art, e.g., distillation, chromatography, precipitation, and selective sorption. Non-limiting examples of such mixtures may contain the following:

| Hydrocarbon Type | Mole % | Preferred Mole % |
| --- | --- | --- |
| Internal olefins | >74 | >90 |
| Vinylidenes | <8.8 | <6.0 |
| Alpha-Oefins | <21 | <5.0 |
| Tri-substituted internal olefin | <4.0 | <2.0 |
| Di-substituted internal olefin | >96 | >98 |

Metathesis Catalysts:

The above-described metathesis reaction is conducted in the presence of a catalytically effective amount of a metathesis catalyst. The term "metathesis catalyst" includes any catalyst or catalyst system which catalyzes the metathesis reaction.

Any known or future-developed metathesis catalyst may be used, alone or in combination with one or more additional catalysts. Exemplary metathesis catalysts include catalysts based upon transition metals, for example, ruthenium, molybdenum, osmium, chromium, rhenium, and tungsten, as well as any suitable metathesis catalyst that is highly selective to the formation of linear internal olefins having low amounts of tri-substitution as described herein. See, e.g., Gibson, T.; Tulich, L. J. Org. Chem. 1981, 46, 1821-1823, Doyle, G. J. Cat. 1973, 30, 118-127, Spronk, R.; Mol, J. C. Applied Catalysis 1991, 70, 295-306 and Fox, H. H.; Schrock, R. R.; O'Dell, R. Organometallics 1994, 13, 635-639, Olefin Metathesis and Metathesis Polymerization by Ivin and Mol (1997), and Chemical and Engineering News, vol. 80, no. 51, Dec. 23, 2002, pp. 29-33, the contents of which are incorporated by reference herein for their disclosures of metathesis catalysts that may be useful in the practice of the present disclosure. Illustrative examples of suitable catalysts include ruthenium and osmium carbene catalysts as disclosed by U.S. Pat. Nos. 5,342,909, 5,312,940, 5,728,917, 5,750,815, 5,710,298, 5,831,108 and 5,728,785, all of which are incorporated herein by reference.

In certain embodiments, the metathesis catalyst is preferably a Group 8 transition metal complex having the structure of formula (III)

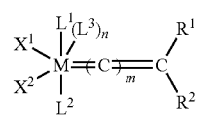

in which the various substituents are as follows:

M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are each independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups,
wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

Moreover, any of the catalyst ligands may further include one or more functional groups. Examples of suitable functional groups include but are not limited to hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

Preferred catalysts contain Ru or Os as the Group 8 transition metal, with Ru being particularly preferred.

Numerous embodiments of the catalysts useful in the reactions of the disclosure are described in more detail below. For the sake of convenience, the catalysts are described in groups, but it should be emphasized that these groups are not meant to be limiting in any way. That is, any of the catalysts useful in the disclosure may fit the description of more than one of the groups described herein.

A first group of catalysts, then, are commonly referred to as 1$^{st}$ Generation Grubbs-type catalysts, and have the structure of formula (III). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are tri-substituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or $-C=C(CH_3)_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as $2^{nd}$ Generation Grubbs-type catalysts, have the structure of formula (III), wherein $L^1$ is a carbene ligand having the structure of formula (IV)

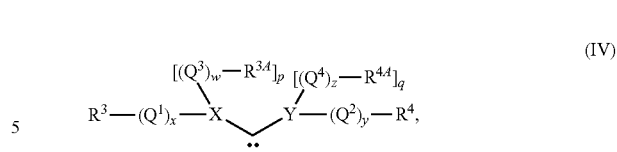

such that the complex may have the structure of formula (V)

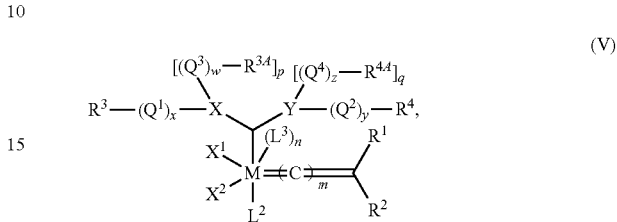

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand is an heterocyclic carbene and preferably an N-heterocyclic carbene, such as the N-heterocyclic carbene having the structure of formula (VI):

where $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not limited to, the following:

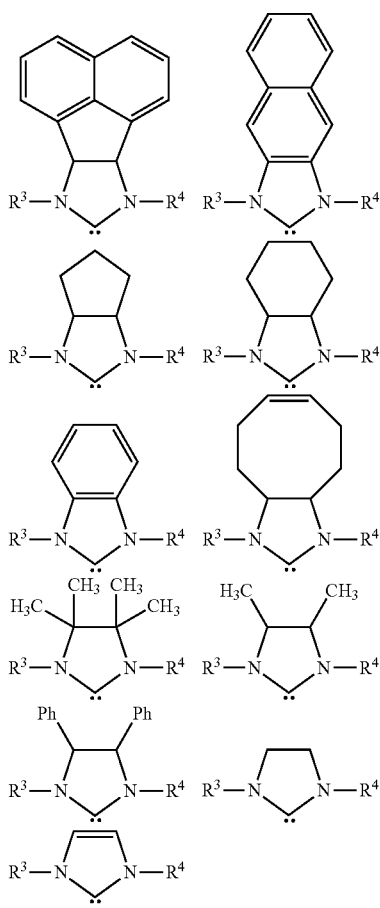

When M is ruthenium, then, the preferred complexes have the structure of formula (VII):

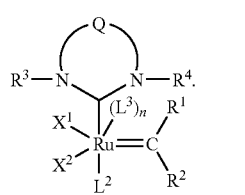

(VII)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl.

In a third group of catalysts having the structure of formula (III), M, m, n, $X^1$, $X^2$, $R^1$, and $R^2$ are as defined for the first group of catalysts, $L^1$ is a strongly coordinating neutral electron donor ligand such as any of those described for the first and second groups of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isoxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VIII)

(VIII)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (III), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As (Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$ (CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to $O_2C(CH_2)_2P(Ph)(CH_2)_2P(Ph)(CH_2)_2CO_2$, phthalocyanines, and porphyrins.

Complexes wherein $L^2$ and $R^2$ are linked are examples of the fourth group of catalysts, and are commonly called "Hoveyda-Grubbs" catalysts. Examples of Hoveyda-Grubbs-type catalysts include the following:

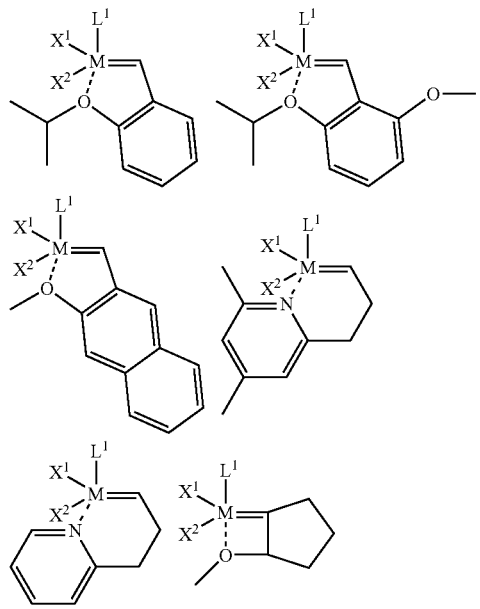

wherein $L^1$, $X^1$, $X^2$, and M are as described for any of the other groups of catalysts.

In addition to the catalysts that have the structure of formula (III), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14, are tetra-coordinated, and are of the general formula (XII)

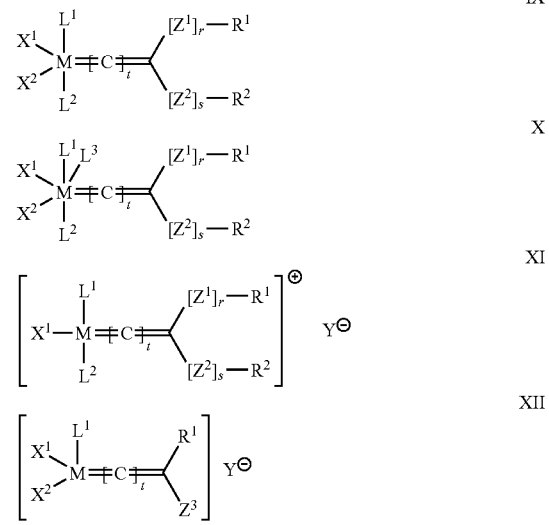

wherein: $X^1$, $X^2$, $L^1$, $L^2$, n, $L^3$, $R^1$, and $R^2$ are as defined for any of the previously defined four groups of catalysts; r and s are independently zero or 1; t is an integer in the range of zero to 5;

Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3$+ or —N($R^2$)$_3$+; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

Other suitable complexes include Group 8 transition metal carbenes bearing a cationic substituent, such as are disclosed in U.S. Pat. No. 7,365,140 (Piers et al.) having the general structure (XIII):

(XIII)

wherein:
M is a Group 8 transition metal;
L1 and L2 are neutral electron donor ligands;
X1 and X2 are anionic ligands;
R1 is hydrogen, C1-C12 hydrocarbyl, or substituted C1-C12 hydrocarbyl;
W is an optionally substituted and/or heteroatom-containing $C_1$-$C_{20}$ hydrocarbylene linkage;
Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;
$Z^-$ is a negatively charged counterion;
m is zero or 1; and
n is zero or 1;

wherein any two or more of $L^1$, $L^2$, $X^1$, $X^2$, $R^1$, W, and Y can be taken together to form a cyclic group.

Each of M, $L^1$, $L^2$, $X^1$, and $X^2$ in structure (XIII) may be as previously defined herein.

W is an optionally substituted and/or heteroatom-containing $C_1$-$C_{20}$ hydrocarbylene linkage, typically an optionally substituted $C_1$-$C_{12}$ alkylene linkage, e.g., —(CH$_2$)$_i$— where i is an integer in the range of 1 to 12 inclusive and any of the hydrogen atoms may be replaced with a non-hydrogen substituent as described earlier herein. The subscript n is zero or 1, meaning that W may or may not be present. In a preferred embodiment, n is zero.

Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Preferably, Y is a $C_1$-$C_{12}$ hydrocarbyl-substituted, positively charged Group 15 or Group 16 element. Representative Y groups include P(R$^2$)$_3$, P(R$^2$)$_3$, As(R$^2$)$_3$, S(R$^2$)$_2$, O(R$^2$)$_2$, where the R$^2$ are independently selected from $C_1$-$C_{12}$ hydrocarbyl; within these, preferred Y groups are phosphines of the structure P(R$^2$)$_3$ wherein the R$^2$ are independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y can also be a heterocyclic group containing the positively charged Group 15 or Group 16 element. For instance, when the Group 15 or Group 16 element is nitrogen, Y may be an optionally substituted pyridinyl, pyrazinyl, or imidazolyl group.

Z$^-$ is a negatively charged counterion associated with the cationic complex, and may be virtually any anion, so long as the anion is inert with respect to the components of the complex and the reactants and reagents used in the metathesis reaction catalyzed. Preferred Z— moieties are weakly coordinating anions, such as, for instance, [B(C$_6$F$_5$)$_4$]$^-$, [BF$_4$]$^-$, [B(C$_6$H$_6$)$_4$]$^-$, [CF$_3$S(O)$_3$]$^-$, [PF$_6$]$^-$, [SbF$_6$]$^-$, [AlCl$_4$]$^-$, [FSO$_3$]$^-$, [CB$_{11}$H$_6$Cl$_6$]$^-$, [CB$_{11}$H$_6$Br$_6$]$^-$, and [SO$_3$F:SbF$_5$]$^-$. Preferred anions suitable as Z$^-$ are of the formula B(R$^{15}$)$_4$— where R$^{15}$ is fluoro, aryl, or perfluorinated aryl, typically fluoro or perfluorinated aryl. Most preferred anions suitable as Z$^-$ are BF$_4^-$ and B(C$_6$F$_5$)$^-$, optimally the latter.

It should be emphasized that any two or more of $X^1$, $X^2$, $L^1$, $L^2$, $R^1$, W, and Y can be taken together to form a cyclic group, as disclosed, for example, in U.S. Pat. No. 5,312,940 to Grubbs et al. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained above.

One group of exemplary catalysts encompassed by the structure of formula (XIII) are those wherein m and n are zero, such that the complex has the structure of formula (XIV):

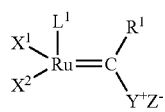

(XIV)

Possible and preferred $X^1$, $X^2$, and $L^1$ ligands are as described earlier with respect to complexes of formula (III), as are possible and preferred Y<+> and Z<-> moieties. M is Ru or Os, preferably Ru, and R$^1$ is hydrogen or $C_1$-$C_{12}$ alkyl, preferably hydrogen.

In formula (XIV)-type catalysts, $L^1$ is preferably a heteroatom-containing carbene ligand having the structure of formula (XV)

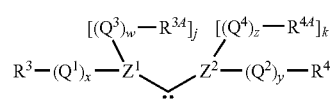

(XV)

such that complex (XIV) has the structure of formula (XVI)

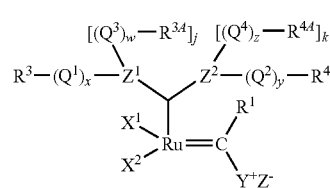

(XVI)

wherein $X^1$, $X^2$, $R^1$, $R^2$, Y, and Z are as defined previously, and the remaining substituents are as follows:

$Z^1$ and $Z^2$ are heteroatoms typically selected from N, O, S, and P. Since O and S are divalent, j is necessarily zero when $Z^1$ is O or S, and k is necessarily zero when $Z^2$ is O or S. However, when $Z^1$ is N or P, then j is 1, and when $Z^2$ is N or P, then k is 1. In a preferred embodiment, both $Z^1$ and $Z^2$ are N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z are independently zero or 1, meaning that each linker is optional. Preferably, w, x, y, and z are all zero.

$R^3$, $R^{3A}$, $R^4$, and $R^{4A}$ are independently selected from hydrogen, hydrogen, $C_1$-$C_{20}$ hydrocarbyl, substituted $C_1$-$C_{20}$ hydrocarbyl, heteroatom-containing $C_1$-$C_{20}$ hydrocarbyl, and substituted heteroatom-containing $C_1$-$C_{20}$ hydrocarbyl.

Preferably, w, x, y, and z are zero, $Z^1$ and $Z^1$ are N, and $R^{3A}$ and $R^{4A}$ are linked to form -Q-, such that the complex has the structure of formula (XVII):

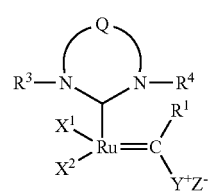

(XVII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q is often, although not necessarily, a two-atom linkage or a three-atom linkage, e.g., —CH$_2$—CH$_2$—, —CH(Ph)-CH(Ph)- where Ph is phenyl; giving rise to an unsubstituted (when R═H) or substituted (R=other than H) triazolyl group; or —CH$_2$—SiR2-CH2- (where R is H, alkyl, alkoxy, etc.).

In a more preferred embodiment, Q is a two-atom linkage having the structure —CR$^8$R$^9$—CR$^{10}$R$^{11}$— or —CR$^8$═CR$^{10}$—, preferably —CR$^8$R$^9$—CR$^{10}$R$^{11}$—, wherein R$^8$, R$^9$, R$^{10}$, and R$^{11}$ are independently selected from hydrogen, C$_1$-C$_{12}$ hydrocarbyl, substituted C$_1$-C$_{12}$ hydrocarbyl, heteroatom-containing C$_1$-C$_{12}$ hydrocarbyl, substituted heteroatom-containing C$_1$-C$_{12}$ hydrocarbyl, and functional groups as defined above. Examples of functional groups include carboxyl, C$_1$-C$_{20}$ alkoxy, C$_5$-C$_{20}$ aryloxy, C$_2$-C$_{20}$ alkoxycarbonyl, C$_2$-C$_{20}$ alkoxycarbonyl, C$_2$-C$_{20}$ acyloxy, C$_1$-C$_{20}$ alkylthio, C$_5$-C$_{20}$ arylthio, C$_1$-C$_{20}$ alkylsulfonyl, and C$_1$-C$_{20}$ alkylsulfinyl, optionally substituted with one or more moieties selected from C$_1$-C$_{10}$ alkyl, C$_1$-C$_{10}$ alkoxy, C$_5$-C$_{20}$ aryl, hydroxyl, sulfhydryl, formyl, and halide. Alternatively, any two of R$^8$, R$^9$, R$^{10}$, and R$^{11}$ may be linked together to form a substituted or unsubstituted, saturated or unsaturated ring structure, e.g., a C$_4$-C$_{12}$ alicyclic group or a C$_5$ or C$_6$ aryl group, which may itself be substituted, e.g., with linked or fused alicyclic or aromatic groups, or with other substituents.

Further details concerning such formula (XIII) complexes, as well as associated preparation methods, may be obtained from U.S. Pat. No. 7,365,140, herein incorporated by reference for its teaching of such complexes and their preparation.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples that may be used in the reactions of the disclosure include the following, some of which for convenience are identified throughout this disclosure by reference to their molecular weight:

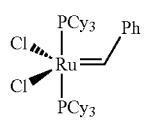
12

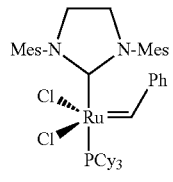
14

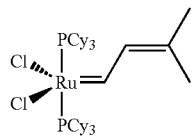
16

-continued

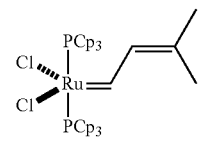
18

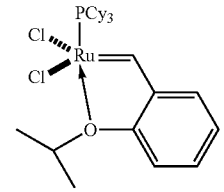
20

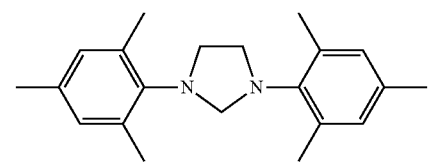
sIMes
22

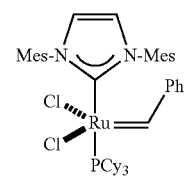
24

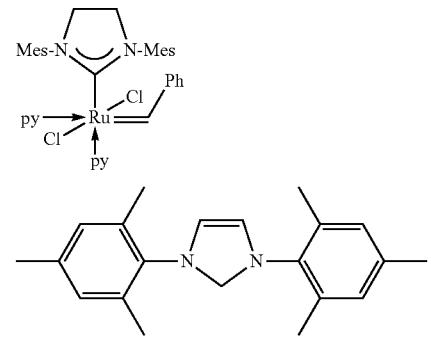
Mes
26

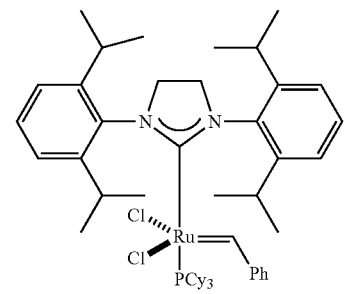
52

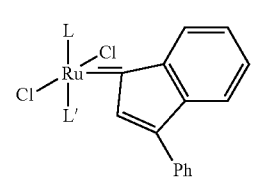
where
L = PCy$_3$, sIMes, Mes, Phobane
L' = PCy$_3$, Phobane

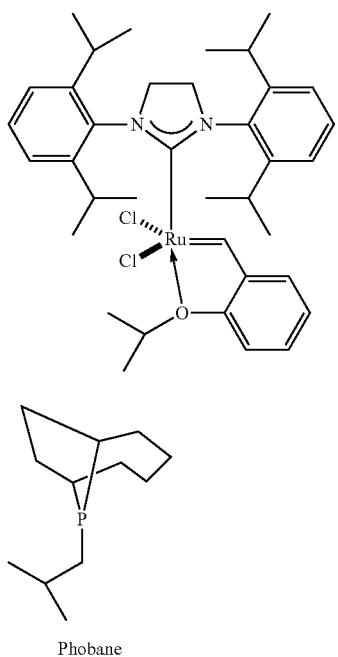
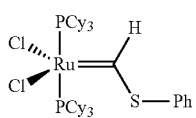
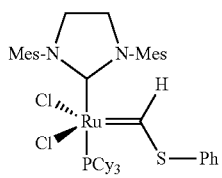
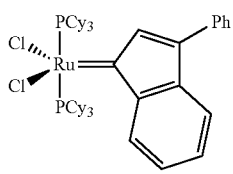
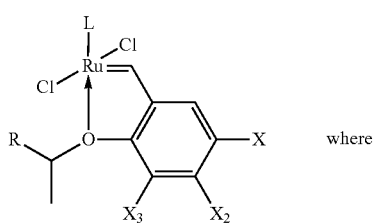
where
L = PCy₃, sIMes, Mes, Phobane
X = H, NO₂, SO₂N(CH₃)₂
$X_2$ = H, N⁺(C₂H₂)₂CH₃
$X_3$ = H, Phenyl
R = H, alkyl, aryl, CO₂Me
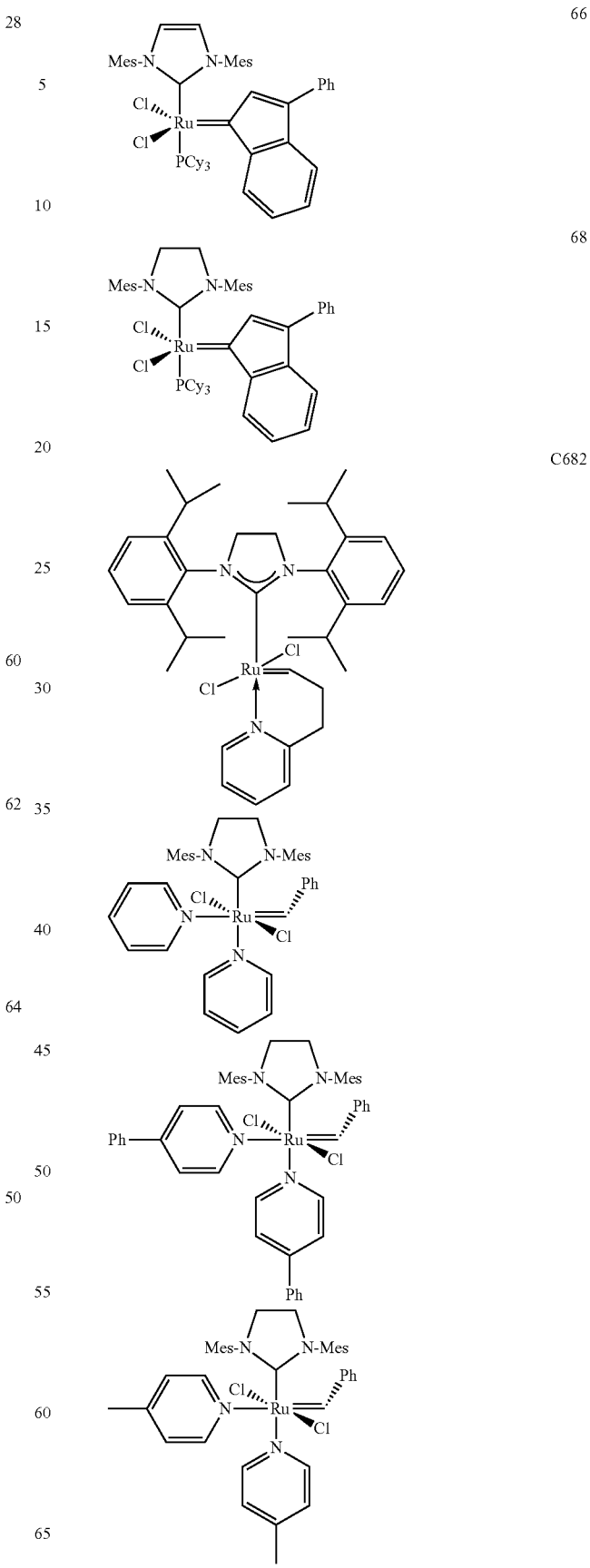

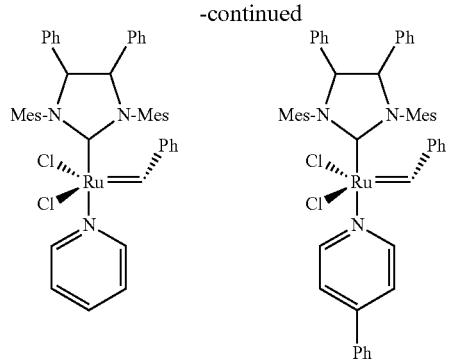
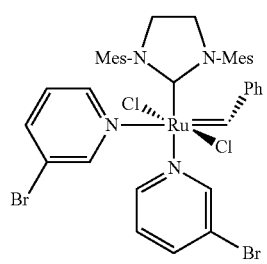
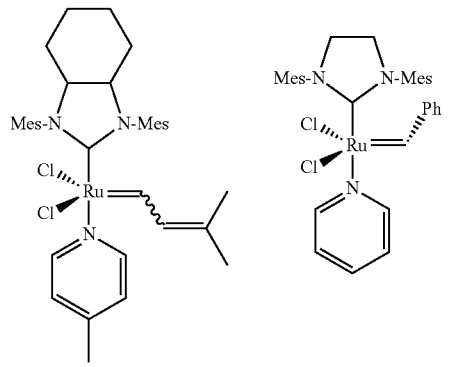
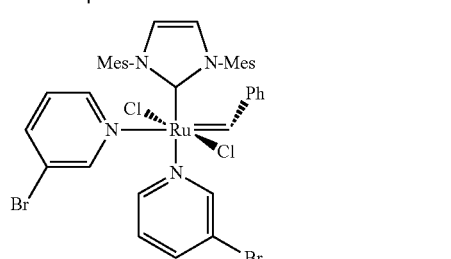
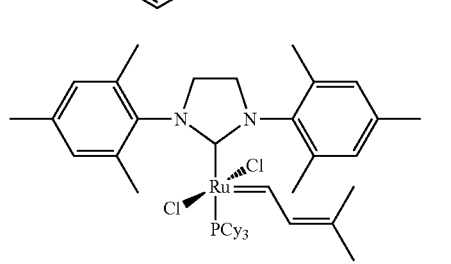
C827
C859
C841-n
C915
C646
C701

27
-continued
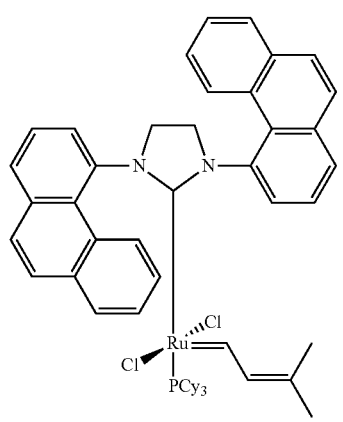
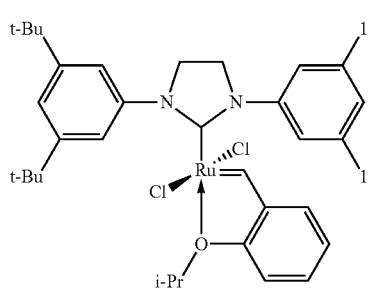
C767-m
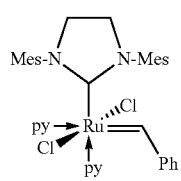
C727
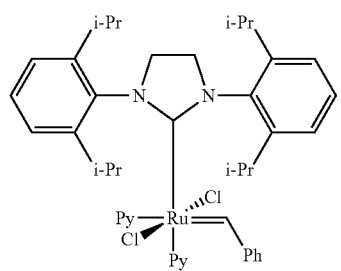
C811
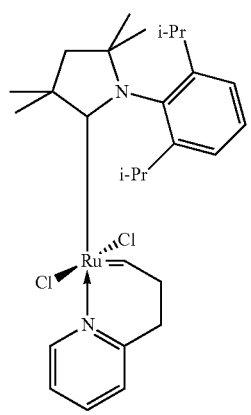
C577
28
-continued
C965-p
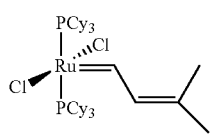
C838
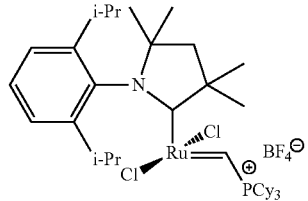
C712
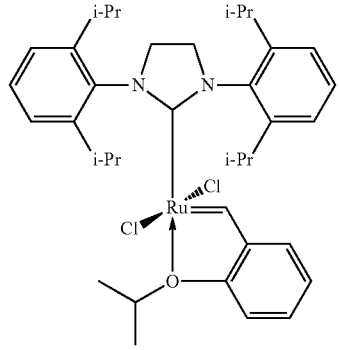
C601
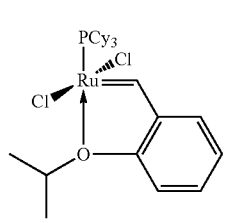
C848
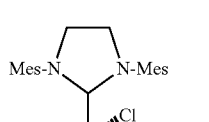
C831
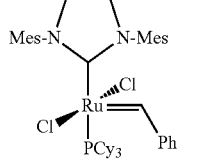
C627
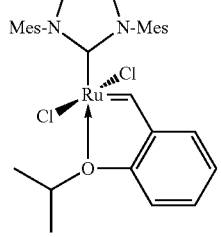

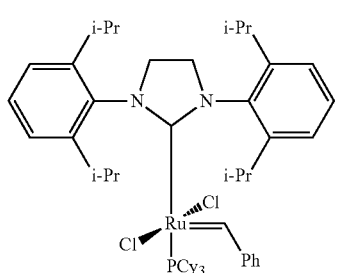
C672
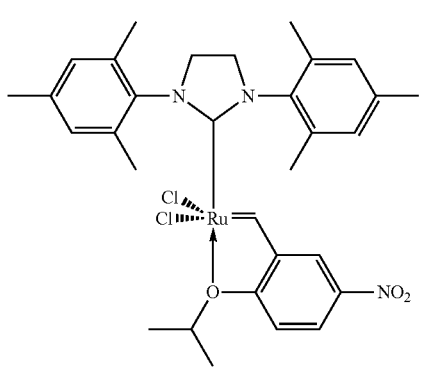
C824
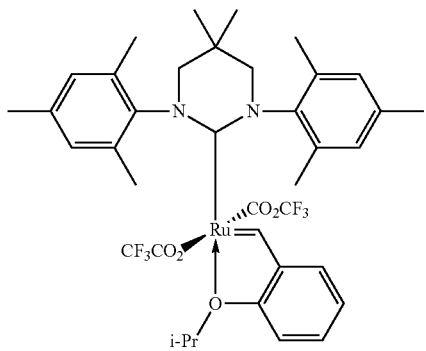
C657
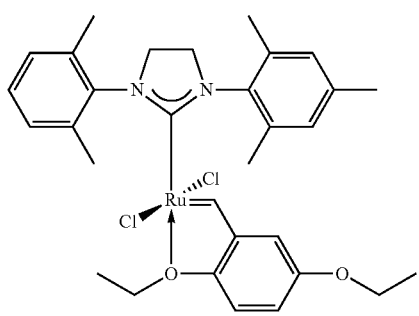
C933
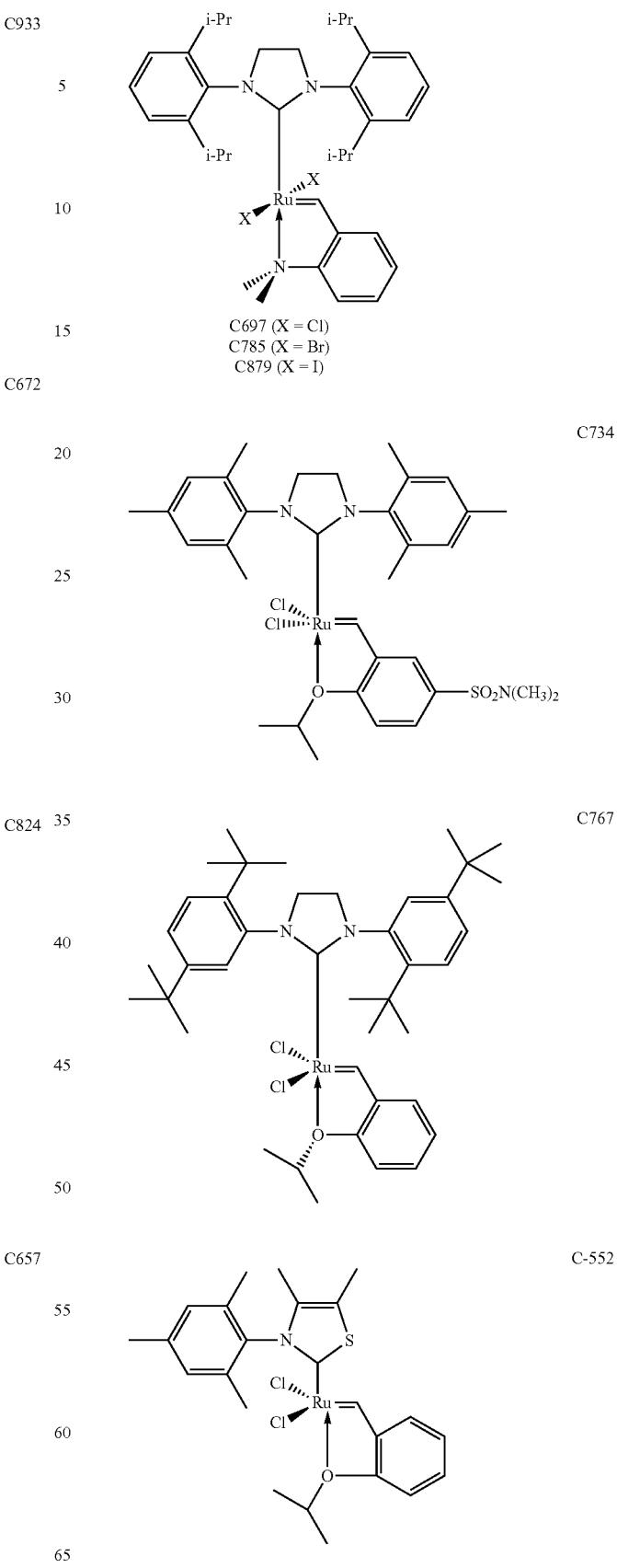

C809
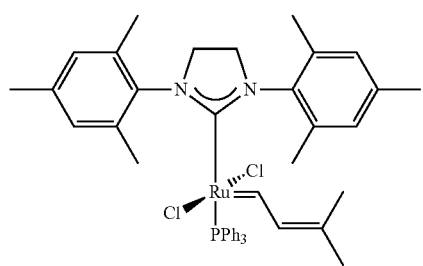
C-566
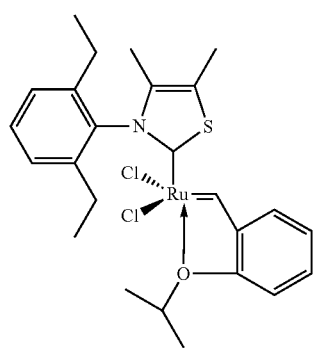
C849
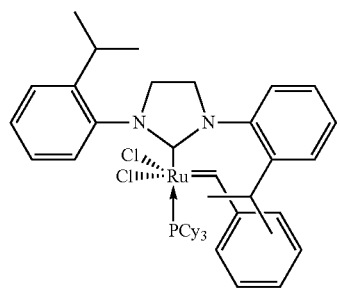
C923
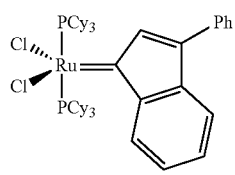
C-524
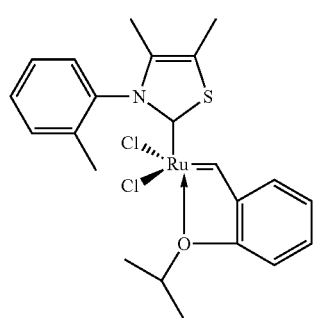
DPA1-278
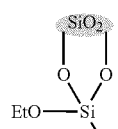
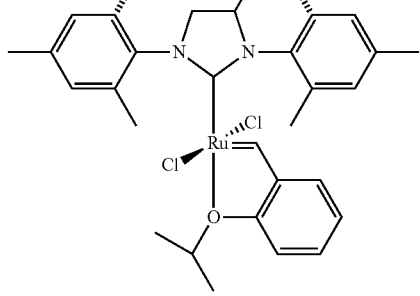
C-598
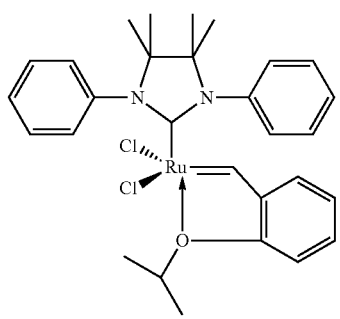
C629
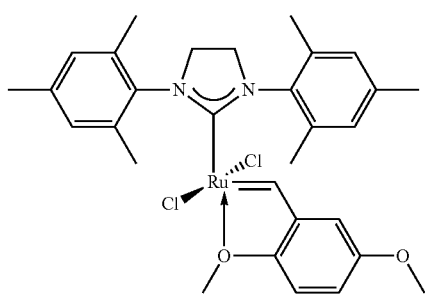
C-626
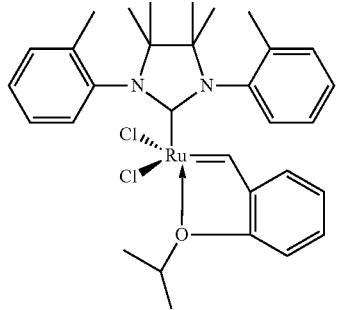

-continued
C833
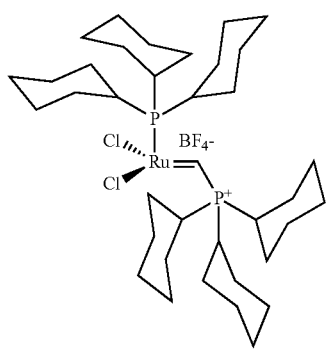
C949
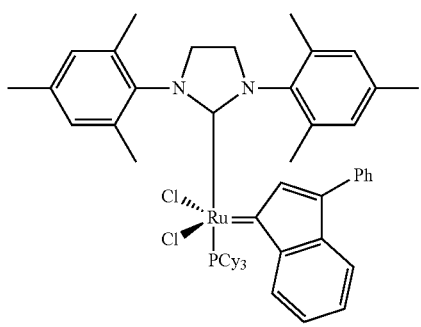
C613
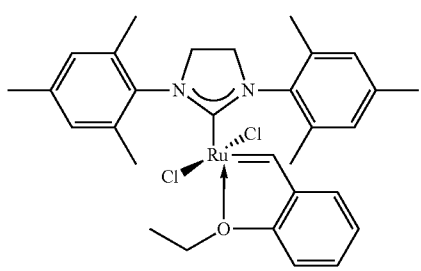
C827
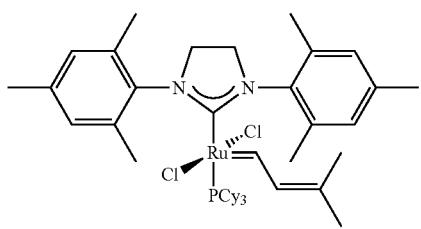
C823
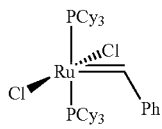
C606
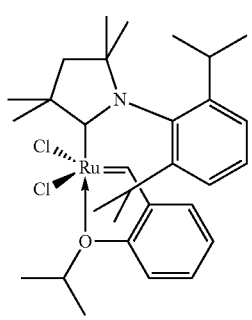
-continued
C627
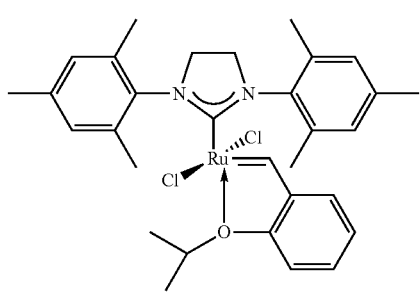
C793
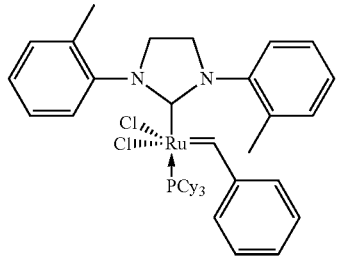
C884
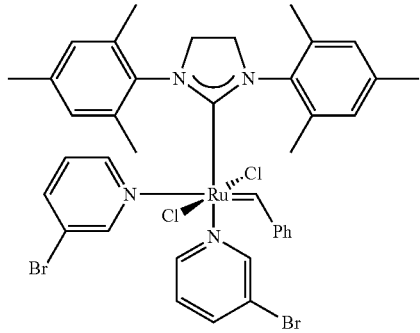
C598Cs
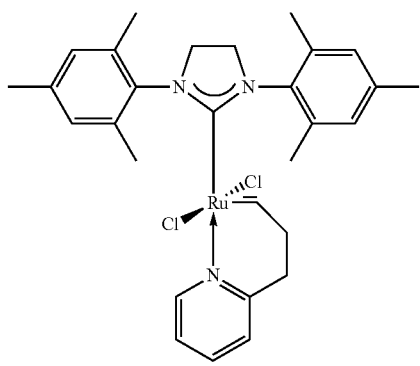
C933
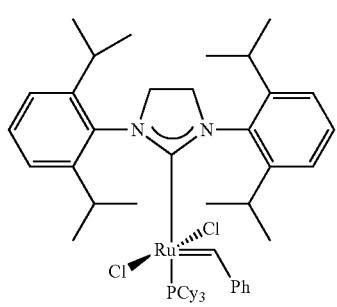

C782

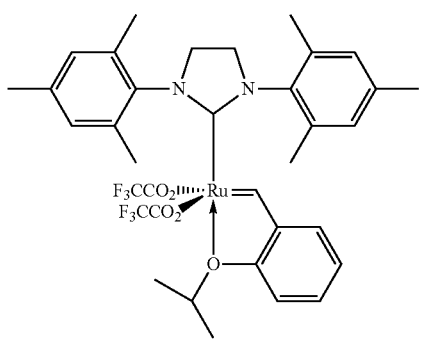

C866

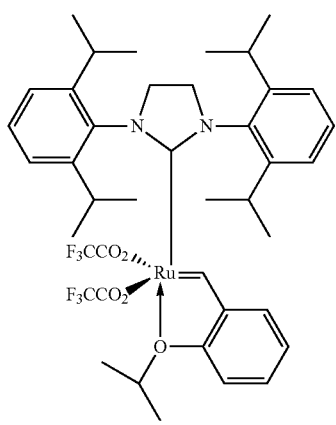

C702

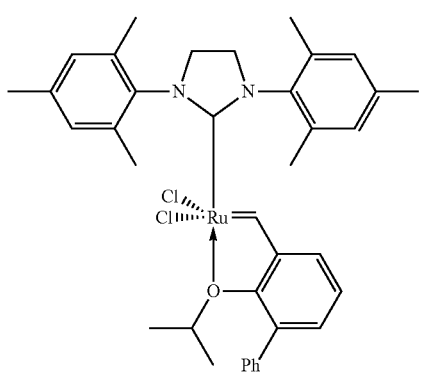

C571

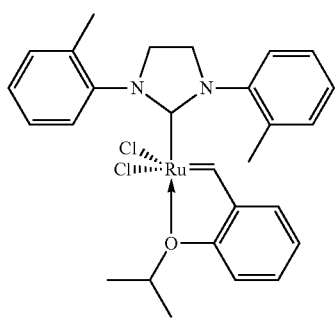

C578

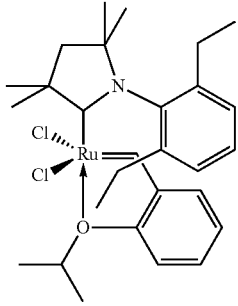

70

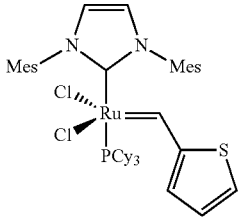

72

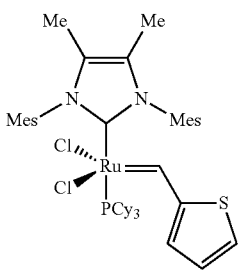

74

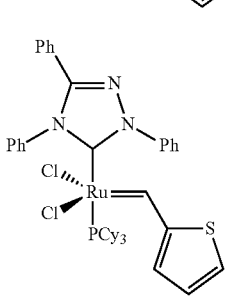

In the foregoing molecular structures and formulae, Ph represents phenyl, Cy represents cyclohexane, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts useful in the reactions of the present disclosure include the following: ruthenium (II) dichloro(3-methyl-1,2-butenylidene)bis(tricyclopentylphosphine) (C716); ruthenium (II) dichloro(3-methyl-1,2-butenylidene)bis(tricyclohexylphosphine) (C801); ruthenium (II) dichloro(phenylmethylene)bis(tricyclohexylphosphine) (C823); ruthenium (II) [1,3-bis-(2,4,6-trimethylphenyl)-2-imidazolidinylidene]dichloro(phenylmethylene)(triphenylphosphine) (C830), and ruthenium (II) dichloro(vinyl phenylmethylene)bis(tricyclohexylphosphine) (C835); ruthenium (II) dichloro(tricyclohexylphosphine)(o-isopropoxyphenylmethylene) (C601), and ruthenium (II) (1,3-bis- (2,4,6-trimethylphenyl)-2-imidazolidinylidene)dichloro (phenylmethylene) (bis 3-bromopyridine (C884)).

Exemplary ruthenium-based metathesis catalysts include those represented by structures 12 (commonly known as Grubbs's catalyst), 14 and 16. Structures 18, 20, 22, 24, 26, 28, 60, 62, 64, 66, 68, 70, 72 and 74 represent additional ruthenium-based metathesis catalysts. Catalysts C627, C682, C697, C712, C831, C915, and C827 represent still additional ruthenium-based catalysts. General structures 50 and 52 represent additional ruthenium-based metathesis catalysts of the type reported in Chemical & Engineering News; Feb. 12, 2007, at pages 37-47. In the structures, Ph is phenyl, Mes is mesityl, py is pyridine, Cp is cyclopentyl, and Cy is cyclohexyl.

Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Publication No. 2007/0004917 A1), all incorporated by reference herein in their entireties. A number of the metathesis catalysts as shown are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

As used herein, a Schrock catalyst means a catalyst as generally described in U.S. Pat. Nos. 4,681,956 and 5,146,033, the contents of which are incorporated by reference herein. Particularly useful as catalysts in the metathesis reaction are the Schrock catalysts having the following general formula:

wherein M is molybdenum or tungsten, and more preferably molybdenum; $R^1$ is alkyl, aryl, or arylalkyl; $R^2$ is alkyl, aryl, arylalkyl or halogen substituted derivatives thereof, particularly preferred is a fluorinated alkyl or fluorinated aryl; and $R^3$ is alkyl, aryl, or arylalkyl. Particularly preferred are those Schrock catalysts containing molybdenum.

Sulfonation

Sulfonation of the internal olefin or mixture of internal olefins may be carried out by any method known to a person skilled in the art. The sulfonation reaction may be typically carried out in a continuous thin film reactor maintained at about 10 to about 50° C. The internal olefin or mixture is placed in the reactor along with sulfur trioxide diluted with air. The molar ratio of internal olefin to sulfur trioxide may be maintained at a suitable ratio, e.g., from about 0.7:1 to about 1.1:1. The sulfonated derivative of internal olefin or mixture may be neutralized with alkali, e.g., sodium hydroxide, to form the corresponding salt. The reaction is exothermic and the viscosity of the reaction product may be dependent on the amount of water present. General conditions and processes for sulfonation of olefins are disclosed in U.S. Pat. No. 4,252,192, the contents of which are incorporated herein.

EOR Process

Processes for enhanced oil recovery, as well as compositions, conditions, process variables, techniques and sequences utilized therein are known and disclosed in U.S. Pat. Nos. 5,247,993, 5,654,261, 6,022,834, 6,439,308, 7,055,602, 7,137,447 and 7,229,950; and in Hirasaki, G.; Miller, C.; Puerto, M.; Recent Advances in Surfactant EOR. *SPE* 2008 (115386), the contents of which are incorporated herein for their teachings relating to EOR techniques.

The present process for enhanced oil recovery from an oil-bearing formation may utilize a chemical enhanced oil recovery technique, alone or in combination with other enhanced oil recovery techniques such as thermal or gas injection enhanced oil recovery.

Surfactant polymer (SP) flooding may involve injecting into a reservoir a fluid containing water and/or brine and from about 0.05 weight percent or even lower to about 2 weight percent or even higher of surfactant and about 0.05 weight percent or even lower to about 1 weight percent or even higher of polymer. It will be understood by those skilled in the art that both surfactant and polymer loadings are dependent on reservoir conditions and on cost considerations. Alkali Surfactant Polymer (ASP) flooding may involve injection of water and/or brine containing alkali in addition to surfactant and polymer. ASP systems may contain on the order of about 0.1 weight percent or even lower to about 1 weight percent or even higher of alkali, about 0.05 weight percent or even lower to about 2 weight percent or even higher of surfactant, and about 0.05 weight percent or even lower to about 1 weight percent or even higher of polymer.

The present process for enhanced oil recovery from an oil-bearing formation may include introducing into said formation an aqueous composition comprising at least one sulfonated derivative of an internal olefin or mixture of internal olefins wherein the internal olefin or mixture is characterized by having low amounts of tri-substitution on the olefin bond. The present disclosure may be carried out using injection and production systems as defined by any suitable arrangement of wells. For illustration purposes, one exemplary well arrangement commonly used in flooding operations and suitable for use in carrying out the oil recovery processes of the present disclosure involves two wells. The SP or ASP flood is injected into one well and oil is recovered from a second adjacent well. Of course, other well arrangements may be used in carrying out the present disclosure.

Co-Surfactants

In some embodiments, co-surfactants may be used in combination with the sulfonated derivative of the internal olefin or mixture of internal olefins. Anionic, nonionic, zwitterionic, amphoteric and cationic surfactants may be employed. Examples of anionic surfactants include: internal olefin sulfonates other than those disclosed herein, e.g., internal olefin sulfonates based on internal olefins having greater than about 6 mole percent tri-substitution on the double bond, alkoxylated alcohol sulfates, alkoxylated alcohol sulfonates, alkylaryl sulfonates, alpha-olefin sulfonates, alkane sulfonates, alkane sulfates, alkylphenol sulfates, alkylamide sulfates, alkylamine sulfates, alkylamide ether sulfates, alkylaryl polyether sulfonates, alkylphenol sulfonates, ligninsulfonates, petroleum sulfonates, phosphates esters, alkali metal, ammonium or amine salts of fatty acids referred to as soaps, fatty alcohol ether sulfates, alkyl-ether carboxylates, N-acyl-N-alkyltaurates, arylalkane sulfonates, sulfosuccinate esters, alkyldiphenylethersulfonates, alkylpapthalenesulfonates, napthalenesulfonic acid-formaldehyde condensates, alkyl isothionates, fatty acid polypeptide condensation products, sulfonated glyceride oils, fatty acid monoethanolamide sulfates, α-sulfonated fatty acid esters, N-acyl glutamates, N-acyl glycinates, N-acyl alinates, acylated amino acids, and fluorinated anionics. Examples of nonionic surfactants include derivatives of the adducts of propylene oxide/ethylene oxide having a molecular weight of from 1000 to 15000, alkoxylated alkylphenols, alkoxylated alcohols, alkoxylated glycols, alkoxylated mercaptans, long-chain carboxylic acid esters, alkanolamine condensates, alkanolamides, tertiary acetylenic glycols, alkoxylated silicones, N-alkylpyrolidones, alkylene oxide copolymers, ethoxylated hydrocarbons, fatty amine oxides, fatty acid glycol partial esters, fatty acid alkanolamides, and alkylpolyglucosides. Examples of zwitterionic and amphoteric surfactants include $C_8$-$C_{18}$ betaines, $C_8$-$C_{18}$ sulfobetaines, $C_8$-$C_{24}$ alkylamido-$C_1$-$C_4$ alkylenebetaines, β-N-alkylminopropionic acids, N-alkyl-β-iminodipropionic acids, imidazoline carboxylates, N-alkylbetaines, amidoamines, amidobetaines, amine oxides, and sulfobetaines. Examples of cationic surfactants include long-chain amines and corresponding salts, acylated polyamines, quaternary ammonium salts, imidazolium salts, alkoxylated long-chain amines, quaternized long-chain amines, and amine oxides.

Solvents

In some embodiments, solvents may be used. Examples of solvents include alcohols, ethers, and amines. More specific examples of solvents are ethyl alcohol, n-propyl alcohol, iso-propyl alcohol, iso-butyl alcohol, n-butyl alcohol, sec-butyl alcohol, n-amyl alcohol, sec-amyl alcohol, hexyl alcohol, octanol, 2-ethylhexyl alcohol and the like, ethylene glycol butylether, lauryl alcohol ethoxylate, glycerin, poly(glycerin), polyalkylene alcohol ethers, polyalkylene glycols, poly(oxyalkylene)glycols, poly(oxyalkylene)glycols ethers or any other common organic solvent or combinations of any two or more solvents.

Polymers

In some embodiments polymers may be used to increase mobilization of at least a portion of the oil through the formation. Suitable polymers include, but are not limited to, polyacrylamides, partially hydrolyzed polyacrylamide, polyacrylates, ethylenic copolymers, biopolymers, carboxymethylcellulose, polyvinyl alcohol, polystyrene sulfonates, polyvinylpyrrolidone, 2-acrylamide-2-methyl propane sulfonate, or combinations thereof. Examples of ethylenic copolymers include copolymers of acrylic acid and acrylamide, acrylic acid and lauryl acrylate, lauryl acrylate and acrylamide. Examples of biopolymers include xanthan gum and guar gum. Molecular weights (Mw) of the polymers may range from about 10,000 daltons to about 20,000,000 daltons. Polymers are used in the range of about 500 to about 2500 ppm concentration, preferably from about 1000 to 2000 ppm in order to match or exceed the reservoir oil viscosity under the reservoir conditions of temperature and pressure. In some embodiments, polymers may be crosslinked in situ in a hydrocarbon containing formation. In other embodiments, polymers may be generated in situ in a hydrocarbon containing formation. Polymers and polymer preparations for use in oil recovery are described in U.S. Pat. Nos. 6,427,268, 6,439,308, 5,654,261, 5,284,206, 5,199,490 and 5,103,909, all of which are incorporated by reference herein.

Alkali

Sodium hydroxide, sodium carbonate, sodium bicarbonate, sodium metaborate, and sodium tetraborate are non-limiting examples of alkali that may be employed in the practice of the present disclosure. It will be understood by those skilled in the art that basic salts of other Group 1A metals and Group 2A metals may serve as a suitable counter ion for the role of alkali. It will also be understood by those skilled in the art that basic organic alkali compounds such as, but not limited too, ethanolamine, triethanolamine, or ethylenediamine tetraacetic acid, amines in general, as well as any other compounds that raise pH and thus would create soaps in situ sodium salt, may serve the role of alkali in the present disclosure. Furthermore, any technique that neutralizes acids present in the oil may be employed.

The EOR composition of the disclosure may be manufactured, stored and shipped in concentrate form for subsequent dilution with water or brine to form an injectable fluid. As a concentrate, the EOR composition may typically contain from about 15 to about 85 wt. % water, from about 15 to about 85 wt. % sulfonated derivative of an internal olefin or mixture of internal olefins as disclosed herein, and from about 0 to about 50 wt. % optional components. The foregoing amounts are for illustrative purposes only. The amounts of water, surfactant and optional components employed may vary widely depending on such variables as salinity, crude oil composition, temperature, formation, and the like. It is well within the purview of one skilled in the art to select appropriate amounts for each component based on the particular set of variables that may be encountered in a specific oil-bearing formation. Upon dilution with water or brine, from about 0.01 to about 5, preferably from about 0.05 to about 1 wt. %, of the EOR composition of the disclosure, based on the total weight of the injectable fluid, may be introduced to an oil-bearing formation.

In some embodiments of the disclosure, optimal salinity may be decreased by increasing alpha-olefin (AO) conversion of the metathesis-derived internal olefin which is subsequently sulfonated and employed in a formulation for chemical EOR.

One skilled in the art will recognize that modifications may be made in the present disclosure without deviating from the spirit or scope of the disclosure. The disclosure is illustrated further by the following examples which are not to be construed as limiting the disclosure or scope of the specific procedures described herein.

the liquid. The nitrogen was vented through the condenser into a glycerin filled bubbler. The liquid was heated to temperature and was degassed for 0.5 hour at 60° C. or 1 hour at 30° C. (see Table 1) with a constant subsurface flow of nitrogen. Afterwards, 100 mole ppm (based on total moles of olefin employed) of metathesis catalyst (see Table 1) was added by removing the thermocouple and adding as quickly as possible under a positive nitrogen pressure. The nitrogen flow was continued throughout the remainder of the reaction, and the reaction was monitored by $^1$HNMR spectroscopy at various times. Once the reaction had reached a conversion of 97% or greater or had reacted for 24-26 hours, the reaction mixture was cooled to room temperature and filtered through a plug of Purasil (60 Å, 230-400 mesh) in a 350 mL coarse glass fitted funnel. The weight was taken, the filtered sample was analyzed by $^1$HNMR spectroscopy, and its iodine value was determined. The final internal olefin content (provided as a mole percent), iodine values, and calculated equivalent weights are provided in Table 1 below.

TABLE 1

Analytical Data for Internal Olefin Products from Metathesis Procedure A.

| Internal Olefin (IO) | Catalyst Structure of Formula | Temp. (° C.) | Rxn Time (h) | % IO | % αO | % VO | % TO | IV | EW | Conversion (%) |
|---|---|---|---|---|---|---|---|---|---|---|
| A1 | 70 | 60 | 8 | 90.86 | 2.33 | 5.47 | 1.33 | 88.1 | 281.1 | 97.5 |
| A2 | 66 | 60 | 23.5 | 92.26 | 1.08 | 5.1 | 1.57 | 87.1 | 291.4 | 99.0 |
| A3 | 14 | 60 | 4 | 91.87 | 1.32 | 4.91 | 1.91 | 89.1 | 284.9 | 98.6 |
| A4 | 12 | 60 | 26.25 | 81.41 | 12.48 | 6.12 | 0 | 94.8 | 267.9 | 86.7 |
| A5 | C827 | 60 | 6 | 92.35 | 0.88 | 5.02 | 1.75 | 88.6 | 286.4 | 99.1 |
| A6 | 72 | 60 | 3 | 92.29 | 1.16 | 5.82 | 0.74 | 88.6 | 283.2 | 98.8 |
| A7 | 14 | 30 | 24.5 | 91.21 | 1.84 | 5.17 | 1.78 | 87.4 | 290.2 | 97.8 |
| A8 | 14 | 60 | 4.25 | 95.1 | 1.6 | 3.3 | 4.0 | 88.4 | 287.3 | 98.2 |

Example A8 was produced at twice the catalyst loading as example A3. % IO = mole % internal olefin, % αO = mole % α-olefin, % VO = mole % vinylidene, and % TO = mole % tri-substituted olefin, all of which were measured by $^1$HNMR spectroscopy. IV = iodine value in units of g $I_2$ /100 g sample. EW = equivalent weight in g/mole. Percent conversion is defined as the quotient % IO dividend by the sum of % IO and % αO, multiplied by 100.

EXAMPLES

Example 1

General Metathesis Procedure A

A mixture of 1-decene (0.2 moles, NAO 10 from Chevron Phillips Chemical Company), 1-dodecene (0.2 moles, NAO 12 from Chevron Phillips Chemical Company) and 1-tetradecene (0.2 moles, NAO 14 from Chevron Phillips Chemical Company) was placed into a 250 mL four-necked reaction flask equipped with a thermocouple, a magnetic stirbar, a reflux condenser, and rubber septa in the remaining neck. A syringe needle (18 gauge) was inserted through one of the septa and submerged in the liquid. The needle was attached to a nitrogen source and nitrogen was gently bubbled through Example 2

General Metathesis Procedure B for the Synthesis of Internal Olefins (IO) with Ruthenium Catalyst 12

Standard inert atmosphere techniques were employed throughout the metathesis reaction in order to minimize any effects of oxygen on the reaction. The desired alpha-olefin or alpha-olefin mixture ($C_{10}$: 1-decene, $C_{12}$: 1-dodecene, $C_{14}$: 1-tetradecene, or mixtures thereof, obtained from CP Chem, The Woodlands, Tex.) was charged to a 1 L four-necked reaction flask equipped with a thermocouple, magnetic stirbar, reflux condenser, and rubber septa in each of the remaining two necks and heated to 50° C. Addition of a ruthenium-based metathesis catalyst 12 (obtained from Sigma-Aldrich, Inc; Milwaukee, Wis.; Catalog #579726) (ca 0.0.02-0.25 mole %) initiated the reaction. After achieving an olefin conversion of greater than 95% as determined by $^1$HNMR spectroscopy, heating was discontinued and the reaction sparged with air. Filtration through silica gel removed the spent catalyst from the resulting internal olefin. Analytical data for the products are provided in Table 2.

TABLE 2

Analytical Data for Internal Olefin Products from Metathesis Procedure B.

| Example No. | Feed composition | Rxn Time (h) | Cat. (mole %) | mole % IO | mole % αO | mole % VO | mole % TO | IV | EW | Conversion (%) |
|---|---|---|---|---|---|---|---|---|---|---|
| B1 | C10 | 109.75 | 0.25 | 97.29 | 1.07 | 1.64 | 0 | 106.7 | 238.0 | 98.9 |
| B2 | C10, 12 | 144 | 0.25 | 92.9 | 4.28 | 2.84 | 0 | 94.9 | 267.4 | 95.6 |
| B3 | C10, 12, 14 | 45 | 0.24 | 91.0 | 2.4 | 6.6 | 0 | 86.2 | 294.4 | 97.4 |
| B4 | C12, 14 | 126.75 | 0.1 | 90.4 | 2.2 | 7.4 | 0 | 82.9 | 306.2 | 97.2 |
| B5 | C10, 14 | 71 | 0.1 | 92.7 | 1.06 | 6.2 | 0 | 86.8 | 292.5 | 98.9 |
| B6 | C14 | 24.75 | 0.1 | 88.9 | 2.3 | 8.8 | 0 | 76.0 | 334.0 | 97.5 |
| B7 | C10, 12 | 104 | 0.13 | 94.0 | 0.5 | 5.80 | 0 | 93.5 | 271.5 | 98.8 |
| B8 | C14 | 171.5 | 0.1 | 93.0 | 0.6 | 6.4 | 0 | 87.0 | 291.8 | 99.3 |
| B9 | C10 | 168 | 0.1 | 95.8 | 0.8 | 3.4 | 0 | 100.2 | 253.3 | 99.2 |
| B10 | C14, 16 | 96 | 0.02 | 88.5 | 2.7 | 8.8 | 0 | 75.0 | 338.5 | 97.0 |

C10 = 1-decene. C12 = 1-dodecene. C14 = 1-tetradecene, C16 = 1-hexadecene.
Components of the feed composition are in equal molar concentrations. Percent conversion is defined as in Table 1.

Example 3

Metathesis Procedure C for the Scale-Up Synthesis of Internal Olefins with Ruthenium Catalyst C831

The starting material was passed through an activated alumina column and loaded into a 50 gallon reactor. The reactor was evacuated by mechanical vacuum pump (with outgassing vented through a fume hood) and refilled with argon or nitrogen three times. Catalyst (0.00005 equiv.) was added as a solid through the reactor port under a positive pressure of nitrogen. The reactor was closed, and the solution was stirred under vacuum. After several minutes, vigorous foaming began. The process was run in two stages. In stage one (2-3 h), the temperature was set at 20° C. and full vacuum was applied. In stage two (17-23 h), the temperature was increased to 30° C. and vacuum was accompanied by sparging $N_2$ (diverted from a bubbler) through a dip tube. The reaction was monitored by GC at the completion of stage one, two hours into stage two, and at the reaction end point. Monitoring was accomplished by closing the reactor to vacuum, backfilling with $N_2$, and sampling under a positive pressure of $N_2$. Upon completion, the product was pumped from the reactor, filtered through silica gel, and the colorless oil was collected. The product analysis is provided in Table 3.

TABLE 3

Analysis of the product from metathesis procedure C.

| Example No. | Feed Composition | % IO | % αO | % VO | % TO | IV | EW | Conversion (%) |
|---|---|---|---|---|---|---|---|---|
| C1 | C10, 12, 14 | 90.5 | 3.1 | 4.8 | 1.6 | 85.5 | 296.9 | 96.7 |

Components of the feed composition are in equal molar concentrations. % IO = mole % internal olefin, % αO = mole % α-olefin, % VO = mole % vinylidene, and % TO = mole % tri-substituted olefin, all of which were measured by $^1$HNMR spectroscopy. IV = iodine value in units of g $I_2$/100 g sample. EW = equivalent weight in g/mole. Percent conversion is defined as table 1.

Example 4a

Falling Film Sulfonation of the Product from Procedure C

One gallon of the product from Procedure C was sulfonated with a dry air/$SO_3$ mixture on a 6 ft, 0.5" (ID) diameter falling film sulfonator at a feed flow rate of 200 g/minute and feed temperature of 25° C. The $SO_3$/air mixture was at a temperature of 40° C. and a flow rate of 61.27 g/minute. The product exited the tube at 44° C. The sulfonated, acidic product was then neutralized by pouring into a precooled (17° C.) solution of 1.93 lbs of 50 wt. % NaOH (aq) in 3.79 lbs of water and 1.43 lbs of Butylcellosolve® over approximately 12 minutes. At the end of the neutralization, an additional 330 g of acid was added to deplete excess caustic. The temperature rose to 41.2° C. at the end of the neutralization. The neutralized solution was then heated overnight at ca 95° C. under a nitrogen blanket yielding 5 quarts of sulfonated product. Actives=52.38 wt. %. Free caustic=0.44 wt. %. Solids=60.02 wt. %. Table 5 contains analytical data for internal olefin sulfonates generated in this patent.

Example 4b

Falling Film Sulfonation of the Comparative Internal Olefins Comp IO-1, Comp IO-2A, Comp IO-2B Internal olefin feed was continuously sulfonated using a falling film reactor with three 1 inch ID tubes. The feed was delivered to the reactor tubes at a temperature of 25° C. and a rate of between 187 and 190 lbs/h split evenly between each tube. The feed was co-currently reacted with a 40° C. gas stream mixture containing dry air delivered at rate of 167 SCFM, and sulfur trioxide added at a rate of between 60 and 63 lbs/h. The annulus of the reactor tubes contained a cooling media delivered at 22° C. The resulting acid product was continuously added to a neutralizer unit in which the acid was mixed with:

50 wt. % sodium hydroxide added at a rate of 64.8 lbs/h
    Water added at a rate of 28.7 lbs/h
    Butylcellosolve® added at a rate of 25.0 lbs/h
    A continuously circulating stream consisting of the neutralized mixture of these materials.

These streams were mixed utilizing a high speed mixer consisting of a rotor and stator. The circulating stream was maintained at a temperature between 35 and 40° C. The product from this unit (containing a slight excess of unreacted sodium hydroxide) was collected and charged to a batch reaction vessel. After the head space was purged with nitrogen, the closed vessel was heated such that the resulting pressure in the reactor was between 18 and 20 PSIG; this occurred at a temperature between 111 and 115° C. The reactor was held at temperature until the free caustic content of the mixture stabilized. This typically required approximately eight hours at temperature.

Example 5

Metathesis Procedure D for the Synthesis of Internal Olefin Mixtures with Ruthenium Catalyst C831

Representative procedure for sample preparation: A 3-neck 1-L round bottomed flask with magnetic stir bar was charged with 300 g of the C10/12/14 AO blend. The flask was evacuated (internal pressure at either 0.5 or 75 mm Hg) and the system was warmed to 30° C. Catalyst C831 (2.5-25 mole ppm) was added as a solution in toluene (5-20 mL) via syringe, at which point gas evolution was observed. The reaction was allowed to proceed under vacuum for 14-22 h undisturbed. The flask was then backfilled with nitrogen and the crude product was filtered through a pad of silica gel. Products were colorless liquids and were analyzed by GC and $^1$HNMR spectroscopy. Analytical data for each of the products is provided in Table 4.

examples. The mole % di-substituted olefin is defined as the quotient of one half the integrated intensity of the region associated with the two protons attached to the double bond divided by the sum of one half the integrated intensity of region associated with the two protons attached to the double bond and the integrated intensity of region associated with the proton attached to the tri-substituted double bond multiplied by 100. See FIGS. 5 and 6a-d for an explanation of the spectral interpretation as well as representative spectra. Table 6 contains a summary of the results. All of the metathesis-derived internal olefins have less than about four mole percent and typically less than one mole percent tri-substitution. Table 6a provides descriptions of comparative isomerization-derived internal olefins. Comp IO-2A and Comp IO-2B are different lots of the same material. The amount of tri-substitution present in the isomerization-derived internal olefins is at least greater than about six mole percent.

TABLE 5

Summary of Analytical Data on Internal Olefin Sulfonates

| IO Feed | IOS Example # | Actives[1] (wt. %) | Free Caustic[2] (wt. %) |
|---|---|---|---|
| A8 | IOS-01 | 54.6 | 0.5 |
| B9 | IOS-02 | 66.8 | 0.5 |

TABLE 4

Analytical Data for Samples Produced at Varying Levels of Internal Olefin Concentrations Using Procedure D.

| Example No. | mole % IO | mole % αO | mole % VO | mole % TO | IO (wt %)[a] | IV | EW (g/mole) | Conversion (%)[b] |
|---|---|---|---|---|---|---|---|---|
| D1 | 43.7 | 51.8 | 4.4 | 0 | 56.6 | 109.42 | 232.0 | 45.7 |
| D2 | 51.8 | 43.7 | 4.5 | 0 | 64.4 | 105.89 | 239.7 | 54.2 |
| D3 | 61.4 | 33.3 | 5.3 | 0 | 72.7 | 98.55 | 257.5 | 64.8 |
| D5 | 73.7 | 20.6 | 5.6 | 0 | 82.9 | 93.92 | 270.2 | 78.1 |
| D6 | 84.5 | 9.2 | 5.6 | 0.7 | 89.5 | 88.41 | 287.1 | 90.2 |

[a]The weight percent of internal olefin was determined by gas chromatography and is a composite of all internal olefins present in the product.
[b]Conversion is defined as in Table 1.

Example 6

Sulfonation Procedure for Internal Olefins Made by General Metathesis Procedure B, C, or D Lab-scale sulfonations were carried out by contacting the internal olefins prepared by procedure B, C or D with about a 25% molar excess (based on iodine value) of sulfur trioxide at 35-40° C. in a stirred 500 mL reactor. Immediately following the sulfonation step, the acid was added to a stirred solution of water, 50 wt. % NaOH (1.3 equivalents based on acid), and Butylcellosolve® (10 wt. % based on acid) while maintaining a temperature below 45° C. After stirring for 1 h, the contents of the flask were transferred to a 400 mL Parr® reactor and stirred for 1.5 h at 150° C. to yield the final internal olefin sulfonate product. Tables 5 and 5a contain analytical data and descriptions of internal olefin sulfonates generated herein. Quantification of Substitution in Internal Olefins $^1$HNMR spectroscopy was used to determine the amount of substitution on the double bond for internal olefins that are the object of the disclosure as well as those of the comparative TABLE 5-continued Summary of Analytical Data on Internal Olefin Sulfonates

| IO Feed | IOS Example # | Actives[1] (wt. %) | Free Caustic[2] (wt. %) |
|---|---|---|---|
| B3 | IOS-04 | 65.1 | 0.1 |
| B4 | IOS-10 | 61.8 | 0.1 |
| B5 | IOS-09 | 65.1 | 0.1 |
| B7 | IOS-03 | 65.2 | 0.1 |
| B8 | IOS-16 | 61.3 | 0.1 |
| B10 | IOS-11 | 43.4 | 0.7 |
| C1 | IOS-06A | 50.4 | 0.8 |
| C1 | IOS-06B | 52.4 | 0.4 |
| D1 | IOS-14 | 47.3 | 0.6 |
| D3 | IOS-13 | 48.3 | 0.3 |
| D5 | IOS-12 | 50.8 | 0.4 |
| D6 | IOS-15 | 47.2 | 0.6 |
| Comp IO-2A[3] | C-IOS-10 | 61.4 | 0.1 |
| Comp IO-2A[3] | C-IOS-03 | 70.1 | 0.3 |
| Comp IO-1[4] | C-IOS-11 | 60.9 | 0.3 |
| Comp IO-2B[5] | C-IOS-12 | 62.5 | 0.1 |
| Comp IO-1[4] | C-IOS-01 | 64.9 | 1.1 |

TABLE 5-continued

Summary of Analytical Data on Internal Olefin Sulfonates

| IO Feed | IOS Example # | Actives[1] (wt. %) | Free Caustic[2] (wt. %) |
|---|---|---|---|
| Comp IO-2B[5] | C-IOS-06 | 68.3 | 0.3 |
| Comp IO-2A[3] | C-IOS-09 | 62.2 | 0.5 |
| Comp IO-1[4] | C-IOS-02 | 64.2 | 0.2 |

[1]Actives determined by potentiometric titration of anionic surfactants. This method is based on ASTM D 4251-83.
[2]Free caustic determined by titration with HCl to neutrality and expressed in terms of wt. % NaOH.
[3]Comp IO-2A is C2024 internal olefin available from Shell Chemical. It is a distinct lot from Comp IO-2B.
[4]Comp IO-2B is C2024 internal olefin available from Shell Chemical. It is a distinct lot from Comp IO-2A.
[5]Comp IO-1 is Isomerized Alpha Olefin C20-24 available from Chevron Phillips Chemical.

Example 7

Experimental Procedure for Determination of Optimal Salinity (OS)

This procedure is adapted from those available in the literature. See, Levitt, D. B.; Jackson, A. C.; Heinson, C.; Britton, L. N.; Malik, T.; Dwarakanath, V.; Pope, G. A., Identification and Evaluation of High Performance EOR Surfactants. *SPE* 2006, (100089), 1-11, Levitt, D. B. Experimental Evaluation of High Performance EOR Surfactants for a Dolomite Oil Reservoir. University of Texas, Austin, 2006, Zhao, P.; Jackson, A. C.; Britton, C.; Kim, D. H.; Britton, L. N.; Levitt, D. B., Development of High-Performance Surfactants for Difficult Oils. *SPE* 2008, (113432), the contents of which are incorporated by reference herein for their teachings of techniques for determination of optimal salinity.

Solutions containing:
  2 wt % surfactant (internal olefin sulfonate and optionally Petrostep® C-8 present at 20 wt. % of the total 2 wt. % surfactant)
  4 wt % solvent (Butylcellosolve® from Dow Chemical)
  1 wt % alkali ($Na_2CO_3$) (optional)

were prepared at NaCl brine concentrations varying from 0.00 to 6.00 wt. %. The formulation without the optional Petrostep® C-8 and sodium carbonate is defined here as the Single Component Formulation in Table 6, while the formulation containing both the optional Petrostep® C-8 and sodium carbonate is defined here as the Dual Component Formulation. Petrostep® C-8 is the sodium salt of branched dodecylbenzene sulfonate, available commercially from the Stepan Company. Known volumes of these solutions were then added to graduated glass tubes, placed in contact with an excess amount of oil (decane in the case of the Single Component Formulation; dodecane in the case of the Dual Component Formulation), sealed, and allowed to equilibrate at 50° C. for two weeks. Noting the relative volumes of the resulting aqueous, organic, and microemulsion phases allows the determination of solubility ratios for each formulation-oil pair at a given brine concentration. From this data, one skilled in the art can determine the optimal salinity of a formulation against the tested oil. The data collected in these experiments is summarized in Table 6. FIGS. 1 through 4 demonstrate that formulations containing internal olefin sulfonates derived from internal olefins characterized by having low amounts of tri-substitution about the double bond exhibit lower optimal salinities than those containing internal olefin sulfonates derived from internal olefins with comparable median carbon numbers and higher degrees of substitution. It is worth noting that IOS-02, which has a median carbon number of C18 and a low degree of substitution about the double bond, provides an optimal salinity comparable to or lower than materials with higher degrees of substitution but higher median carbon numbers. This is unexpected, as a higher carbon number should produce a more hydrophobic surfactant and therefore a lower optimal salinity. Also noteworthy is the fact that IOS-01, with a degree of substitution of about four mole percent, has a lower optimal salinity than formulations based on IOS's derived from IO's having a slightly higher degree of substitution of about six mole percent. The data shown in FIGS. 1 through 4 and Table 6 in terms of both effect and magnitude are surprising and unexpected.

TABLE 5a

IOS Descriptions

[1]IOS: example of the disclosure
[2]C-IOS: comparative example
[3]Sulfonated according to the procedure in example 6
[4]Sulfonated according to the procedure in example 4a
[5]Sulfonated according to the procedure in example 4b Example 8

The Effect of IO Conversion on Optimal Salinity (OS)

Internal olefin sulfonates (IOS) prepared using the method outlined in Example 6 with the internal olefins (IO) described in Table 4 were evaluated in formulations against decane and dodecane according to the procedure described in Example 9 to determine the effect of alpha-olefin conversion on performance (FIGS. 11 and 12). Both formulations showed a reduction of optimal salinity with increasing alpha-olefin (AO) conversion. One possible explanation for this behavior is that the AO remaining in the IO product is sulfonated along with the IO and decreases the hydrophobicity of the surfactant formulation owing to its smaller carbon number and lower molecular weight.

TABLE 6

Summary of Optimal Salinities and Internal Olefin Compositions

| | IO Composition (mole %) | | | Optimal Salinity (wt. % NaCl) | |
|---|---|---|---|---|---|
| | | | | Single | Dual |
| IO Feed | Di-substituted | Tri-substituted | IOS Name | Component[1] Formulation | Component[1] Formulation |
| A8 | 96.0 | 4.0 | IOS-01 | 0.52 | 1.61 |
| B9 | 100 | 0.0 | IOS-02 | 1.33 | 3.24 |

TABLE 6-continued

Summary of Optimal Salinities and Internal Olefin Compositions

| | | | | Optimal Salinity (wt. % NaCl) | |
| --- | --- | --- | --- | --- | --- |
| | IO Composition (mole %) | | | Single | Dual |
| IO Feed | Di-substituted | Tri-substituted | IOS Name | Component[1] Formulation | Component[1] Formulation |
| B7 | 100 | 0.0 | IOS-03 | 0.89 | 1.66 |
| B3 | 100 | 0.0 | IOS-04 | 0.35 | 1.18 |
| C1 | 97.2 | 2.8 | IOS-06A | 0.70 | 1.27 |
| C1 | 97.2 | 2.8 | IOS-06B | 0.56 | 0.61 |
| B8 | 100 | 0.0 | IOS-08 | N/D | 1.52 |
| B5 | 100 | 0.0 | IOS-09 | 0.52 | 1.25 |
| B4 | 100 | 0.0 | IOS-10 | N/D | 0.71 |
| B10 | 100 | 0.0 | IOS-11 | N/D | 1.13 |
| Comp IO-1 | 79.7 | 20.3 | C-IOS-01 | N/D | 4.33 |
| Comp IO-1 | 79.7 | 20.3 | C-IOS-02 | 2.61 | 4.65 |
| Comp IO-2A | 94.0 | 6.0 | C-IOS-03 | 2.27 | 3.20 |
| Comp IO-2B | 90.9 | 9.1 | C-IOS-06 | 2.41 | 3.58 |
| Comp IO-2A | 94.0 | 6.0 | C-IOS-09 | 2.06 | N/D |
| Comp IO-2A | 94.0 | 6.0 | C-IOS-10 | 2.29 | 4.24 |
| Comp IO-1 | 79.7 | 20.3 | C-IOS-11 | 2.86 | N/D |
| Comp IO-2B | 90.9 | 9.1 | C-IOS-12 | N/D | 4.05 |

[1]See Example 7

TABLE 6a

Summary of Comparative Isomerization-Derived Internal Olefins.

| IO | Name | Source |
| --- | --- | --- |
| Comp IO-1 | Isomerized Alpha Olefin C20-24 | Chevron Phillips |
| Comp IO-2A | ENORDET ® 0241 | Shell Chemical |
| Comp IO-2B | ENORDET ® 0241 | Shell Chemical |

Example 9

Measurement of Interfacial Tension (IFT) and Determination of Optimal Salinity (OS) by Spinning-Drop Tensiometry and Phase Tube Observations Against Crude Oils Surfactant test mixtures were made up as shown in Table 7. Table 10 contains a list of the crude oils used as well as characterizational data. The number in the formulation in Table 7 corresponds to the number of the oil listed in Table 10 with which the formulation was used. Where possible, phase tubes observations were used to determine the optimal salinity and IFT according to methods described in the references cited in Example 7. In cases where the opacity of the oil obscured phase behavior the IFT was measured between the surfactant solution and the oil interface at different salinities using a spinning-drop tensiometer. The results of these experiments are presented in FIG. 7. The lowest IFT values occur at the optimal salinity of the system, and both low optimal salinity and interfacial tension are desirable. The data shown in FIG. 7, demonstrate that internal olefin sulfonates derived from internal olefins possessing a low degree of tri-substitution about the double bond display low IFT's (i.e. less than $1 \times 10^{-2}$ mN/m) at optimal salinity against actual crude oils, and therefore have utility in EOR formulations.

Example 10

ASP Core-Flood Experimental Procedure

The core-flooding procedures described below are well known to those skilled in the art and are based on techniques found in the literature (Levitt, D. B. (2006). Experimental Evaluation of High Performance EOR Surfactants for a Dolomite Oil Reservoir. Petroleum Engineering. Austin, University of Texas. Master of Science in Engineering: 160.). The core was prepared in the following manner. A known mass of quartz sand having particle sizes between 100 and 200 mesh was packed into a 11.4" long, 1.5" ID (2" OD) aluminum tube between two 200 mesh stainless-steel screens. The core appa-

TABLE 7

Summary of Phase Behavior Experiment Formulations[1]

| Formulation | Surfactant | Conc. (wt. %) | Co-surfactant | Conc. (wt. %) | Co-surfactant | Conc. (wt. %) | Co-surfactant | Conc. (wt. %) | Co-solvent | Conc. (wt. %) |
| --- | --- | --- | --- | --- | --- | --- | --- | --- | --- | --- |
| 1 | IOS-06B | 0.40 | Petrostep ® S-2 | 0.20 | Petrostep ® A-6 | 0.20 | Petrostep ® C-8 | 0.20 | Neodol ® 25-12 | 0.20 |
| 2 | IOS-06B | 0.30 | Petrostep ® S-2 | 0.20 | Petrostep ® A-6 | 0.20 | Petrostep ® ES-65A | 0.30 | Neodol ® 25-12 | 0.25 |
| 3 | IOS-06B | 0.40 | Petrostep ® S-2 | 0.20 | Petrostep ® A-6 | 0.20 | Petrostep ® C-8 | 0.20 | Neodol ® 25-12 | 0.25 |
| 4 | IOS-06B | 0.40 | Petrostep ® S-2 | 0.10 | Petrostep ® A-6 | 0.50 | None | 0 | EGBE | 0.25 |

[1]All formulations contained 1.0 wt. % Na$_2$CO$_3$. Petrostep ® S-2 is a C1518 internal olefin sulfonate, sodium salt. Petrostep ® A-6 is an alkylaryl sulfonate, sodium salt. Petrostep ® C-8 is a branched alkylaryl sulfonate, sodium salt. All Petrostep ® products are available from the Stepan company. Neodol ® 25-12 is a C1215 12-mole ethoxylate available from Shell Chemical. EGBE stands for ethylene glycol butylether.

ratus was weighed and fixed vertically so that all liquids could be injected from the top. The core was then saturated with de-gassed synthetic produced brine (22,615 ppm total dissolved solids (TDS), see Table 8 for composition) at a flow rate of 2 mL/minute. The mass of the brine necessary to saturate the core was used to calculate the pore volume (PV) of the core. The brine permeability of the core was calculated from the steady-state pressure across the core under a constant brine flow rate. The effluent from subsequent steps was collected using a fraction collector, and the collected fractions were analyzed to determine the relative amounts of oil and water as well as surfactant concentration where appropriate. The core was subsequently flooded with filtered Oil 1 at a rate of 1 mL/minute until the amount of water in the collected fractions became negligible (i.e. <about 0.5 wt. %). A mass balance was performed at this point and the results used to calculate the initial water saturation ($S_{wi}$) after oil saturation and original oil in place (OOIP). OOIP is calculated from $S_{wi}$ (OOIP=PV×(1−$S_{wi}$)). The water-flooding portion of the core-flood commenced upon introduction of synthetic produced brine to the core at a rate of 2 ft/day. The eluted fractions were collected and analyzed for oil and water composition until the amount of oil became negligible (i.e. <about 0.5 wt. %). The total amount of oil displaced by the water was used to determine the residual oil saturation after water-flooding ($S_{or}$).

The ASP-flooding portion of the core-flood commenced upon introduction 0.3 PV of a surfactant solution based on Formulation 1 described in Table 7 at a total surfactant concentration of 0.5 wt. % in a solution of 1 wt. % $Na_2CO_3$, and 2000 ppm HPAM 3630S in 22,615 ppm TDS softened produced water to the core at a rate of 2 ft/day. This was followed by 2-3 PV of a solution of 2000 ppm HPAM 3630S in 11,308 ppm TDS produced water at an injection rate of 2 ft/day. The polymer solution injection continued until the amount of oil in the effluent fractions became negligible (i.e. <about 0.5 wt. %).

TABLE 8

Synthetic Produced Brine Used in the Core-flood Experiment for Oil 1

| Ions | Unit | Injection Water |
|---|---|---|
| $Na^+$ | ppm | 7,951 |
| $Ca^{++}$ | ppm | 298 |
| $Mg^{++}$ | ppm | 193 |
| $Ba^{++}$ | ppm | 7.2 |
| $Cl^-$ | ppm | 12,259 |
| $HCO_3^-$ | ppm | 1,863 |
| $SO_4^{--}$ | ppm | 44 |
| TDS | ppm | 22,615 |

The information and results for the core-flood experiment is shown in Table 9. The residue water saturation after oil saturation step is 0.037 for test formulation IOS-6B.

TABLE 9

Information for the Core-Flood Experiment for IOS-6B

| Property | Unit | Result |
|---|---|---|
| Length | Inch | 11.40 |
| Porosity | % | 44.9 |
| Pore Volume (PV) | mL | 147.22 |
| Total dry mass | g | 378.12 |
| Brine permeability | mD | 3152 |
| $S_{wi}$ after oil saturation[1] | N/A | 0.037 |

TABLE 9-continued

Information for the Core-Flood Experiment for IOS-6B

| Property | Unit | Result |
|---|---|---|
| $S_{or}$ after waterflood[2] | N/A | 0.51 |
| Recovery of $S_{or}$ by ASP | % | 93.62 |
| Surfactant retention[3] | mg/g rock | 0.142 |

[1]$S_{wi}$ is calculated from the percent by weight of water remaining in the core after oil saturation (e.g. 0.036 means 3.6 wt. % of the brine remains after oil flooding).
[2]$S_{or}$ is calculated from the percent by oil of oil remaining in the core after water saturation (e.g. 0.52 means 52 wt. % of the oil remains after water flooding).
[3]Surfactant retention is calculated by determining the amount of surfactant present in eluted fraction by potentiometric titratration (method based on ASTM D 4251-83) and subtracting this quantity from the total amount of surfactant contacted with the core.

TABLE 10

Characterization of Crude Oils

| Property | Unit | Oil 1 | Oil 2 | Oil 3 | Oil 4 |
|---|---|---|---|---|---|
| API gravity | ° | 17.4 | 20.7 | 15.0 | 17.0 |
| TAN (Total Acid Number) | mg KOH/g oil | 1.2 | 0.6 | 0.7 | 0.5 |

At the end of the waterflooding stage, the residual oil is 0.51. FIG. 8 shows the oil recovery of OOIP. The first 2.2 PV is attributed to the waterflood, and the rest to the ASP and polymer flood. The recovery of OOIP is 47%. However, ASP and polymer flooding with solution based on Formulation 1 recovered an additional 50% OOIP. The oil recovery of residue oil ($S_{or}$) in ASP step is shown in FIG. 9. The solution based on Formulation 1 recovered 93 wt. % residual oil in the ASP portion of the flood. The surfactant concentration in the effluent is shown in FIG. 10. The surfactant retentions is low (i.e. 0.142 mg/g rock).

Based on the phase behavior tests and spinning-drop tensiometry, formulations containing surfactant IOS-06B of the instant disclosure consistently displayed both low interfacial tension values at optimal salinities against heavy oils. A formulation based on surfactant IOS-06B of the instant disclosure also recovered a significant amount of residual oil (i.e. 93%) in the ASP portion of a core-flood test. The data shown in FIGS. 8, 9, and 10 demonstrate the utility of the surfactants of the instant disclosure in EOR applications.

What is claimed is:

1. A process for recovering oil from an oil-bearing formation comprising introducing into said formation an aqueous composition comprising at least one surfactant comprising a sulfonated derivative of one or more internal olefins, said sulfonated derivative being obtained by sulfonating a composition comprising internal olefins of the formula:

$R^1R^2C\!\!=\!\!CR^3R^4$ 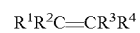

wherein $R^1$, $R^2$, $R^3$ and $R^4$ are the same or different and are hydrogen or straight or branched-chain, saturated hydrocarbyl groups and the total number of carbon atoms of $R^1$, $R^2$, $R^3$ and $R^4$ is 6 to 44 with the proviso that at least about 96 mole percent of $R^1$ and $R^3$ are straight- or branched-chain, saturated hydrocarbyl groups and at least about 96 mole percent of $R^2$ and $R^4$ are hydrogen.

2. The process of claim 1 wherein the internal olefins are obtained by the metathesis of one or more alpha-olefins in the presence of metathesis catalyst.

3. The process of claim 2 wherein the alpha-olefins correspond to the formula:

$R^5HC\!\!=\!\!CH_2$ 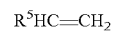

wherein $R^5$ is a straight-chain or branched-chain $C_3$-$C_{22}$ hydrocarbyl group.

4. The process of claim 3 wherein less than about six mole percent of $R^5$ contains alkyl branching.

5. The process of claim 2 wherein the metathesis catalyst is selected from the group consisting of Grubbs-type catalysts, Schrock catalysts, Hoveyda-Grubbs, tungsten catalysts, molybdenum catalysts and rhenium catalysts.

6. The process of claim 2 wherein the metathesis catalyst is of the formula:

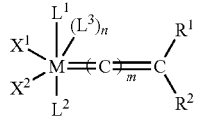

wherein:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are each independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

7. The process of claim 1 wherein at least about 97 mole percent of $R^1$ and $R^3$ are straight- or branched-chain, saturated hydrocarbyl groups and at least about 97 mole percent of $R^2$ and $R^4$ are hydrogen.

8. The process of claim 1 wherein at least about 98 mole percent of $R^1$ and $R^3$ are straight- or branched-chain, saturated hydrocarbyl groups and at least about 98 mole percent of $R^2$ and $R^4$ are hydrogen.

9. The process of claim 1 wherein at least about 99 mole percent of $R^1$ and $R^3$ are straight- or branched-chain, saturated hydrocarbyl groups and at least about 99 mole percent of $R^2$ and $R^4$ are hydrogen.

10. The process of claim 1 wherein less than about six mole percent of $R^1$ and $R^3$ contain alkyl branching.

11. The process of claim 1 wherein the aqueous composition comprises at least one of co-surfactant, solvent, polymer or alkali.

12. The process of claim 1 wherein the oil is a waxy crude oil.

13. A process for enhanced oil recovery from an oil-bearing formation comprising introducing into said formation an aqueous composition comprising at least one surfactant comprising a sulfonated derivative of one or more internal olefins, said sulfonated derivative being obtained by sulfonating a composition comprising internal olefins of the formula:

$$R^1R^2C=CR^3R^4$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44 with the proviso that at least about 96 mole percent of $R^1$ and $R^3$ are straight- or branched-chain, saturated hydrocarbyl groups and at least about 96 mole percent of $R^2$ and $R^4$ are hydrogen, with the further proviso that said internal olefins are obtained by the metathesis of alpha-olefins of the formula:

$$R^5HC=CH_2$$

wherein $R^5$ is a straight-chain or branched-chain $C_3$-$C_{22}$ hydrocarbyl group in the presence of metathesis catalyst.

14. The process of claim 13 wherein the metathesis catalyst is selected from the group consisting of Grubbs-type catalysts, Hoveyda-Grubbs, Schrock catalysts, tungsten catalysts, molybdenum catalysts and rhenium catalysts.

15. The process of claim 13 wherein the metathesis catalyst is of the formula:

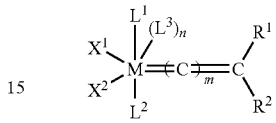

wherein:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are each independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

16. The process of claim 13 wherein at least about 97 mole percent of $R^1$ and $R^3$ are straight- or branched-chain, saturated hydrocarbyl groups and at least about 97 mole percent of $R^2$ and $R^4$ are hydrogen.

17. The process of claim 13 wherein at least about 98 mole percent of $R^1$ and $R^3$ are straight- or branched-chain, saturated hydrocarbyl groups and at least about 98 mole percent of $R^2$ and $R^4$ are hydrogen.

18. The process of claim 13 wherein at least about 99 mole percent of $R^1$ and $R^3$ are straight- or branched-chain, saturated hydrocarbyl groups and at least about 99 mole percent of $R^2$ and $R^4$ are hydrogen.

19. The process of claim 13 wherein less than about six mole percent of $R^1$ and $R^3$ contain alkyl branching.

20. The process of claim 13 wherein less than about six mole percent of $R^5$ contains alkyl branching.

21. A composition for use in recovering oil from an oil-bearing formation comprising:
(i) water;
(ii) at least one surfactant comprising a sulfonated derivative of one or more internal olefins, said sulfonated derivative being obtained by sulfonating a composition comprising internal olefins of the formula:

$$R^1R^2C=CR^3R^4$$

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44 with the proviso that at least about 96 mole percent of $R^1$ and $R^3$ are straight- or branched-chain, saturated hydrocarbyl groups and at least about 96 mole percent of $R^2$ and $R^4$ are hydrogen; and
(iii) optionally one or more additional components.

22. The composition of claim 21 wherein the internal olefins are obtained by the metathesis of one or more alpha-olefins in the presence of metathesis catalyst.

23. The composition of claim 22 wherein the alpha-olefins correspond to the formula:

wherein $R^5$ is a straight-chain or branched-chain $C_3$-$C_{22}$ hydrocarbyl group.

24. The composition of claim 23 wherein less than about six mole percent of $R^5$ contains alkyl branching.

25. The composition of claim 22 wherein the metathesis catalyst is selected from the group consisting of Grubbs-type catalysts, Schrock catalysts, Hoveyda-Grubbs, tungsten catalysts, molybdenum catalysts and rhenium catalysts.

26. The composition of claim 22 wherein the metathesis catalyst is of the formula:

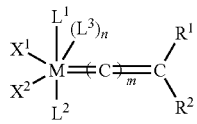

wherein:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are each independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

27. The composition of claim 21 wherein at least about 97 mole percent of $R^1$ and $R^3$ are straight- or branched-chain, saturated hydrocarbyl groups and at least about 97 mole percent of $R^2$ and $R^4$ are hydrogen.

28. The composition of claim 21 wherein at least about 98 mole percent of $R^1$ and $R^3$ are straight- or branched-chain, saturated hydrocarbyl groups and at least about 98 mole percent of $R^2$ and $R^4$ are hydrogen.

29. The composition of claim 21 wherein at least about 99 mole percent of $R^1$ and $R^3$ are straight- or branched-chain, saturated hydrocarbyl groups and at least about 99 mole percent of $R^2$ and $R^4$ are hydrogen.

30. The composition of claim 21 wherein less than about six mole percent of $R^1$ and $R^3$ contain alkyl branching.

31. The composition of claim 21 wherein the optional additional components are selected from the group consisting of co-surfactant, solvent, polymer and alkali.

32. A composition for use in the recovery of oil from an oil-bearing formation, the composition comprising:
(i) water;
(ii) at least one surfactant comprising a sulfonated derivative of one or more internal olefins wherein said internal olefins are obtained via the metathesis of one or more alpha-olefins in the presence of a metathesis catalyst comprising a Group 8 transition metal complex; and
(iii) optionally one or more additional components.

33. A process for recovering oil from an oil-bearing formation which comprises introducing into said formation an aqueous composition comprising at least one surfactant comprising a sulfonated derivative of one or more internal olefins wherein said internal olefins are obtained via the metathesis of one or more alpha-olefins in the presence of a metathesis catalyst comprising a Group 8 transition metal complex.

34. A sulfonated derivative of one or more internal olefins wherein said internal olefins correspond to the formula:

wherein $R^1$, $R^2$, $R^3$ and $R^4$ are the same or different and are hydrogen or straight- or branched-chain, saturated hydrocarbyl groups and the total number of carbon atoms of $R^1$, $R^2$, $R^3$ and $R^4$ is 6 to 44, with the proviso that at least about 96 mole percent of $R^1$ and $R^3$ are straight- or branched-chain, saturated hydrocarbyl groups and at least about 96 mole percent of $R^2$ and $R^4$ are hydrogen in the internal olefins.

35. A sulfonated derivative of one or more internal olefins wherein said internal olefins are obtained via the metathesis of one or more alpha-olefins in the presence of a metathesis catalyst comprising a Group 8 transition metal complex.

36. The sulfonated derivative of claim 35 wherein the metathesis catalyst is of the formula:

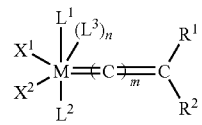

wherein:
M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are each independently anionic ligands; and
$R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

37. The sulfonated derivative of claim 36 wherein $L^1$ is a carbene ligand having the following structure:

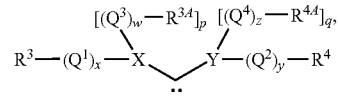

wherein X and Y are heteroatoms selected from the group consisting of N, O, S, and P;
p is zero when X is O or S, q is zero when Y is O or S;
p is 1 when X is N or P;
q is 1 when Y is N or P;
$Q^1$, $Q^2$, $Q^3$, and $Q^4$ are linkers individually selected from the group consisting of —(CO)—, hydrocarbylene, substituted hydrocarbylene, heteroatom-containing hydrocarbylene, and substituted heteroatom-containing hydrocarbylene, wherein two or more substituents on adjacent atoms within $Q^1$, $Q^2$, $Q^3$, and $Q^4$ are optionally linked to form an additional cyclic group;

w, x, y, and z are independently zero or 1;

$R^3$, $R^{3A}$, $R^4$, and $R^{4A}$ are independently selected from the group consisting of hydrogen, hydrocarbyl, substituted hydrocarbyl, heteroatom-containing hydrocarbyl, and substituted heteroatom-containing hydrocarbyl; and and any two or more of $X^1$, $X^2$, $L^1$, $L^2$, $L^3$, $R^1$, $R^2$, $R^3$, $R^{3A}$, $R^4$, and $R^{4A}$ optionally together form a cyclic group, and any one or more of $X^1$, $X^2$, $L^1$, $L^2$, $L^3$, $R^1$, $R^2$, $R^3$, $R^{3A}$, $R^4$, and $R^{4A}$ optionally may be attached to a support.

* * * * *